(12) United States Patent
Sharts et al.

(10) Patent No.: US 6,445,449 B1
(45) Date of Patent: Sep. 3, 2002

(54) METHOD AND APPARATUS FOR DETERMINATION OF CARBON-HALOGEN COMPOUNDS AND APPLICATIONS THEREOF

(75) Inventors: Clay Marcus Sharts, deceased, late of San Diego, CA (US), by Olga Sharts, heiress; Vladimir Semenovich Gorelik, Moscow (RU)

(73) Assignee: San Diego State University, San Diego, CA (US)

( * ) Notice: Subject to any disclaimer, the term of this patent is extended or adjusted under 35 U.S.C. 154(b) by 0 days.

(21) Appl. No.: 09/947,312

(22) Filed: Sep. 5, 2001

Related U.S. Application Data

(63) Continuation of application No. 09/343,148, filed on Jun. 29, 1999, now Pat. No. 6,307,625.
(60) Provisional application No. 60/091,090, filed on Jun. 29, 1998, and provisional application No. 60/138,643, filed on Jun. 10, 1999.

(51) Int. Cl.[7] ............................. G01J 3/44; G01N 21/65

(52) U.S. Cl. ...................................................... 356/301

(58) Field of Search ........................................ 356/301

(56) References Cited

U.S. PATENT DOCUMENTS 3,906,241 A * 9/1975 Thompson .................. 356/301
5,646,425 A  7/1997 Beach ........................ 257/102

OTHER PUBLICATIONS

Laloraya, K., et al., "Laser excited Raman spectrum of 1,1,1–trifluoro–2,2,2–trichloroethane." J. Chem. Phys. vol. 61, No. 5, pp. 1918–1922 (Sep. 1, 1974).

Craig, N., et al., "Vibrational Assignments and Potential Constants for cis– and trans–1,2–Difluoroethylenes and Their Deuterated Modifications." J. Chem. Phys., vol. 51, No. 3, pp. 1127–1142 (Aug. 1, 1969).

Mann, D., et al., "Vibrational Spectrum of Fluorotrichloroethylene." J. Chem. Phys., vol. 23, No. 11, pp. 1989–1992 (Nov. 1955).

Mann, D., et al., "Infrared and Raman Spectra of Trans–Difluorodichloroethylene." J. Chem. Phys., vol. 26, No. 4, pp. 773–779 (Apr. 1957).

Nielsen, J., et al., "Infrared and Raman Spectra of Fluorinated Ethylenes. VI. Fluorotrichloroethylene." J. Chem. Phys., vol. 23, No. 11, pp. 1994–1996 (Nov. 1955).

Nielsen, J., et al., "Raman Spectrum of Gaseous 1–Fluorochloroethylene." J. Chem. Phys., vol. 26, No. 6, pp. 1566–1567 (Jun. 1957).

Korppi–Tommola, J., et al., "The Gas Phase Raman Band Contours of 1,3,5–Trifluorobenzen and the Infrared and Raman Band Contours of 1,3,5–Trifluorobenzene–$d_{3 1,2}$." J. Mol. Spectro., vol. 87, pp. 382–392 (1981).

Da Costa, A., et al., "Raman Spectra and Structure of Perfluorodecanoic Acid and Perfluorodecanoates." Rev. Port. Quim., vol. 26, pp. 154–162 (1984).

(List continued on next page.)

Primary Examiner— F. L. Evans
(74) Attorney, Agent, or Firm—Fish & Richardson P.C.

(57) ABSTRACT

A method and apparatus for determination of fluoroorganic compounds in liquid, gaseous, or crystalline or amorphous solids is based on the detection of carbon-halogen bonds by laser Raman spectroscopy. The method and apparatus provide a general method for detecting and determination of halooorganic compounds. The method and apparatus are applicable in the pharmaceutical industry, in fluorinated drug research and manufacturing; in the medical and clinical studies of the effects of fluoroorganic compounds; in the environmental and agricultural studies and screening, in the analysis of water, soils and air contaminated with fluoroorganic compounds.

58 Claims, 16 Drawing Sheets

OTHER PUBLICATIONS

Blick, K., et al., "Vibrational spectrum and frequency assignments for 2,2–diaminohexafluoropropane." Spectro, Acta., vol. 27A, pp. 777–782 (1991).

Shurvell, H., et al., "The infrared and Raman spectra of pentafluorobenzonitrile." Spectro. Acta., vol. 24A, pp. 1257–1266 (1968).

Crowder, G., et al., "Infrared and Raman spectra of methyl trifluoroacetate." Spectro. Acta., vol. 27A, pp. 1873–1877 (1971).

Berney, C., "Spectroscopy of $CF_3COZ$ compounds—IV Vibrational spectrum of trifluoroacetyl fluoride." Spectro. Acta., vol. 27A, pp. 663–672 (1971).

Miller, F., et al., "The infrared and Raman spectra of hexafluoro–, hexachloro– and hexabromocyclopropane." Spectro. Acta., vol. 23A, pp. 1609–1618 (1967).

Bailey, R., et al., "The vibrational spectra of perfluorotoluene." Spectro. Acta., vol. 24A, pp. 1891–1898 (1968).

Murto, J., et al., "Fluoroalcohols—XX. Infrared and Raman spectra of hexafluoro–2–propanol and its deuterated analogues." Spectro. Acta., vol. 29A, pp. 1121–1137 (1973).

Augdahl, E., et al., "The vibrational spectra of 1–halo–3,3, 3–trifluoropropynes." Spectro. Acta., vol. 29A, pp. 1329–1338 (1973).

Dawson, J., et al., "Infrared spectra of tris(fluoroalkyl)–s–triazines." Spectro. Acta., vol. 23A, pp. 1211–1220 (1966).

Kinumaki, S., et al., "Low Frequency Bands and Barrier to Internal Rotation in Pentafluoroethane." Bull. Chem. Soc. Japan, vol. 41, pp. 809–813 (1968).

Zimmerman, R., et al., "The Vapor–Phase Infrared and Raman Spectra of p–Difluorobenzene ($h_4$) and ($d_4$)." J. Mol. Spectro., vol. 110, pp. 312–325 (1985).

Nielsen, J., et al., "Infrared and Raman Spectra of Fluorinated Ethanes Part XVIII. 1,1,1,2–Tetrafluoroethane." J. Mol. Spectro., vol. 17, pp. 341–347 (1965).

Lunelli, B., et al., "Out–of–Plane Vibrations of 1,2–Difluorobenzene and 1,2–Difluorobenzene–$d_4$." J. Mol. Spectro., vol. 104, pp. 203–207 (1984).

Lunelli, B., et al., "The Vibrational Spectrum of 1,2–Difluorobenzene and 1,2–Difluorobenzene–$d_4$." J. Mol. Spectro., vol. 64, pp. 1–14 (1977).

Zwarich, R., et al., "The Vibrational Spectra of 9–Fluorenone." J. Mol. Spectro., vol. 51, pp. 38–49 (1974).

Kinumaki, S., et al., "Low Frequency Bands and Barrier to Internal Rotation in Pentafluoroethane," Bulletin of the Chemical Society of Japan, vol. 41, pp. 809–813 (1968).

Tuazon, E.C., et al., "Vibrational Spectra of Gaseous 1,1, 1–Trifluoro–2–butyne," The Journal of Chemical Physics, vol. 53, No. 8, pp. 3178–3187 (Oct. 15, 1970).

Harris, W.C., et al, "Interpretation of the vibrational spectral of small ring systems II. Perfluorocyclobutane," The Journal of Chemical Physics, vol. 60, No. 11, pp. 4175–4180 (Jun. 1, 1974).

El Bermani, M.F., et al., "Rotation Isomers of the 1–Fluoro–2–haloethanes," The Journal of Chemical Physics, vol. 49, No. 1, pp. 340–346 (Jul. 1, 1968).

Koenig, J.L., et al., "Raman Scattering and Band Assignments in Polytetrafluoroethylene," The Journal of Chemical Physics, vol. 50, No. 7, pp. 2823–2329 (Apr. 1, 1969).

Craig, N.C., et al., Vibrational Spectra and Assignments for cis– and trans–1,2–Difluorocyclopropane and Three Deuterium Substituted Modifications of Each Isomer, The Journal of Physical Chemistry, vol. 79, No. 21, pp. 2270–2282 (1975).

Craig, N.C., et al., "Infrared and Raman spectra of 1H–trifluorocycloprepene–$d_0$ and –$d_1$," Spectrochimica Acta, vol. 31A, pp. 1463–1473 (1975).

Balfour, W.J., et al., "The i.r. and Raman spectra of propiolyl fluoride and deuterio–propiolyl fluoride," Spectrochimica Acta, vol. 31A, pp. 1085–1091 (1975).

Crowder, G.A., et al., "Vibrational spectra of 2,2–difluoropropane," Spectrochimica Acta, vol. 27A, pp. 2505–2511 (1971).

Faniran, J.A., et al., "The i.r. and Raman spectra of pentafluoroaniline," Spectrochimica Acta, vol. 31A, pp. 1127–1132 (1975).

Shurvell, H.F., et al., "The Infrared and Raman Spectra of Solid Trifluoroacetonitrile," Journal of Molecular Spectroscopy, vol. 33, pp. 436–447 (1970).

Craig, N.C., et al., "Vibrational Assignments for Cis–, Trans–, and Gem–Dichlorofluoroethylenes and Deuterodichlorofluoroethylenes," Journal of Molecular Spectroscopy, vol. 23, pp. 307–319 (1967).

Perettie, D.J., et al., "Infrared and Raman Spectral of Difluoromalononitrile: Vibrational Assignment, Normal Coordinate Analysis and Thermodynamic Functions," Journal of Molecular Spectroscopy, vol. 32, pp. 222–232 (1969).

Lin–Vien, Daimay, et al., The Handbook of "Infrared and Raman Characteristics Frequencies of Organic Molecules," Academic Press, Inc., Chapter 1: Introduction, pp. 1–7 (1991).

Lin–Vien, Daimay, et al., The Handbook of "Infrared and Raman Characteristics Frequencies of Organic Molecules," Academic Press, Inc., Chapter 2: Alkanes, pp. 8–28 (1991).

Lin–Vien, Daimay, et al., The Handbook of "Infrared and Raman Characteristics Frequencies of Organic Molecules," Academic Press, Inc., Chapter 3: Halocompounds, pp. 29–44 (1991).

Lin–Vien, Daimay, et al., The Handbook of "Infrared and Raman Characteristics Frequencies of Organic Molecules," Academic Press, Inc., Chapter 4: Alcohols and Phenols, pp. 45–60 (1991).

Lin–Vien, Daimay, et al., The Handbook of "Infrared and Raman Characteristics Frequencies of Organic Molecules," Academic Press, Inc., Chapter 5: Ethers and Peroxides, pp. 61–72 (1991).

Lin–Vien, Daimay, et al., The Handbook of "Infrared and Raman Characteristics Frequencies of Organic Molecules," Academic Press, Inc., Chapter 6: Alkenes, pp. 73–94 (1991).

Lin–Vien, Daimay, et al., The Handbook of "Infrared and Raman Characteristics Frequencies of Organic Molecules," Academic Press, Inc., Chapter 7: Acetylenes, pp. 95–104 (1991).

Lin–Vien, Daimay, et al., The Handbook of "Infrared and Raman Characteristics Frequencies of Organic Molecules," Academic Press, Inc., Chapter 8: The $-C \equiv N$ and $-N \equiv C$ Groups, pp. 105–115 (1991).

Lin–Vien, Daimay, et al., The Handbook of "Infrared and Raman Characteristics Frequencies of Organic Molecules," Academic Press, Inc., Chapter 9: Compounds Containing the Carbonyl Group, pp. 117–154 (1991).

Lin–Vien, Daimay, et al., The Handbook of "Infrared and Raman Characteristics Frequencies of Organic Molecules," Academic Press, Inc., Chapter 10: Compounds Containing —NH₂, —NHR, and —NR₂ Groups, pp. 155–178 (1991).

Lin–Vien, Daimay, et al., The Handbook of "Infrared and Raman Characteristics Frequencies of Organic Molecules," Academic Press, Inc., Chapter 11: The Nitro Group, pp. 179–189 (1991).

Lin–Vien, Daimay, et al., The Handbook of "Infrared and Raman Characteristics Frequencies of Organic Molecules," Academic Press, Inc., Chapter 12: Double Bonds Containing Nitrogen Atoms, pp. 191–211 (1991).

Lin–Vien, Daimay, et al., The Handbook of "Infrared and Raman Characteristics Frequencies of Organic Molecules," Academic Press, Inc., Chapter 13: Cumulated Double Bonds, pp. 213–224 (1991).

Lin–Vien, Daimay, et al., The Handbook of "Infrared and Raman Characteristics Frequencies of Organic Molecules," Academic Press, Inc., Chapter 14: Organic Sulfur Compounds, pp. 225–250 (1991).

Lin–Vien, Daimay, et al., The Handbook of "Infrared and Raman Characteristics Frequencies of Organic Molecules," Academic Press, Inc., Chapter 15: Organosilicon Compounds, pp. 251–261 (1991).

Lin–Vien, Daimay, et al., The Handbook of "Infrared and Raman Characteristics Frequencies of Organic Molecules," Academic Press, Inc., Chapter 16: Organophosphorus Compounds, pp. 263–276 (1991).

Lin–Vien, Daimay, et al., The Handbook of "Infrared and Raman Characteristics Frequencies of Organic Molecules," Academic Press, Inc., Chapter 17: Aromatic and Heteroaromatic Rings, pp. 277–306 (1991).

* cited by examiner

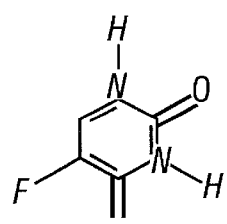
Fluorouracil
(5-FU)
anticancer drug

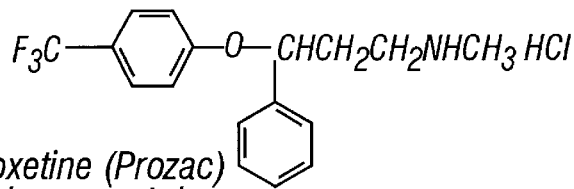
Fluoxetine (Prozac)
antidepressant drug $CF_3CF_2CF_2CF_2CF_2CF_2CF_2CF_2Br$
Perflubron  (Oxygent)
Blood Substitute  (Liquivent)

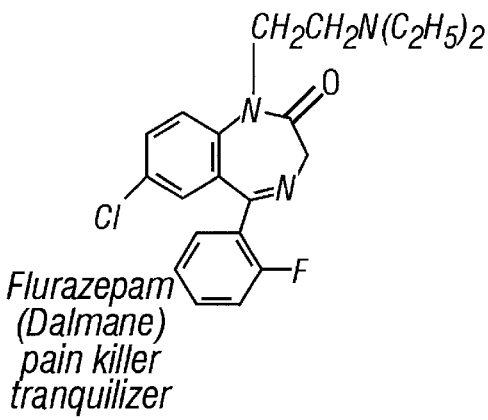
Flurazepam
(Dalmane)
pain killer
tranquilizer

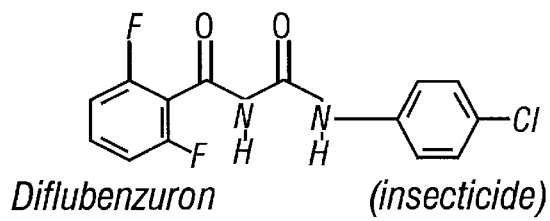
Diflubenzuron  (insecticide)

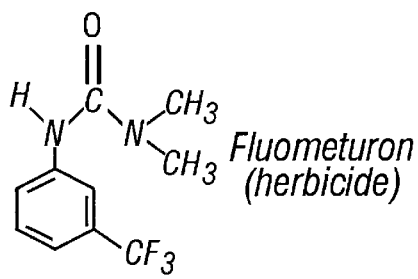
Fluometuron
(herbicide)

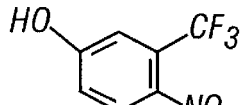
3-Trifluoromethyl-
4-nitrophenol  (lampricide)

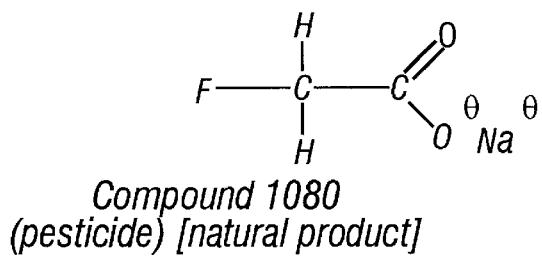
Compound 1080
(pesticide) [natural product]

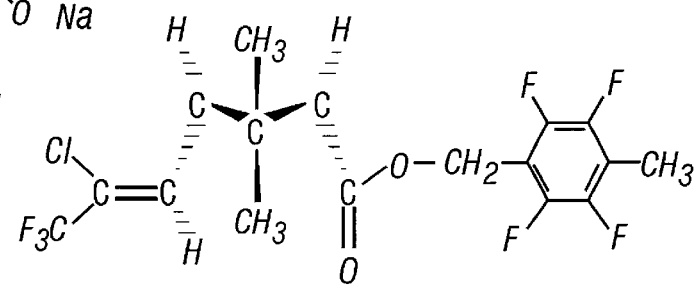
Tefluthrin  PPC 993 (ICI)  Force
(insecticide)

FIG. 9

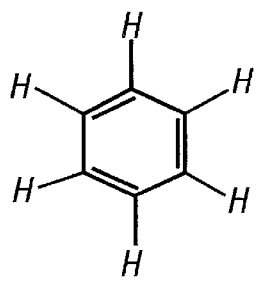
Benzene [$C_6H_6$]
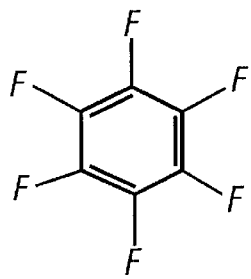
Hexafluorobenzene [$C_6F_6$]
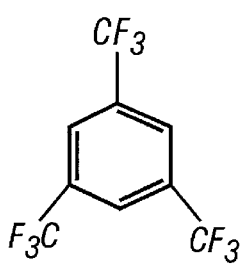
1,3,5-(tris)-Trifluorommethyl-benzene [$C_9F_9H_3$]
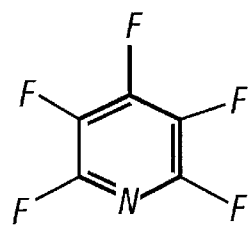
Pentafluoropyridine [$C_6F_5N$]
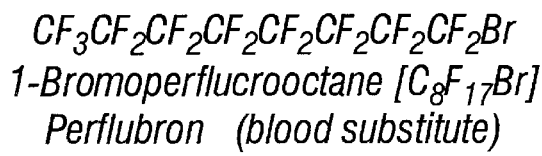
$CF_3CF_2CF_2CF_2CF_2CF_2CF_2CF_2Br$
1-Bromoperflucrooctane [$C_8F_{17}Br$]
Perflubron (blood substitute)
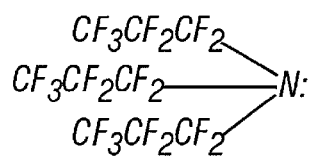
Perfluorotripropylamine [$C_9F_{21}N$]
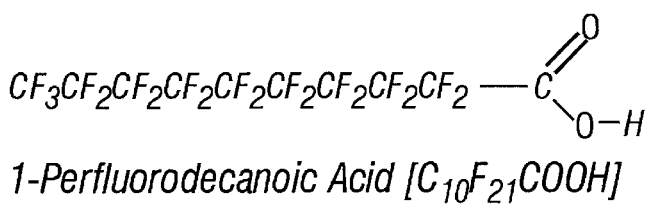
1-Perfluorodecanoic Acid [$C_{10}F_{21}COOH$]
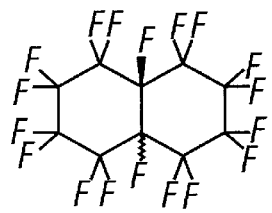
Perfluorodecalin
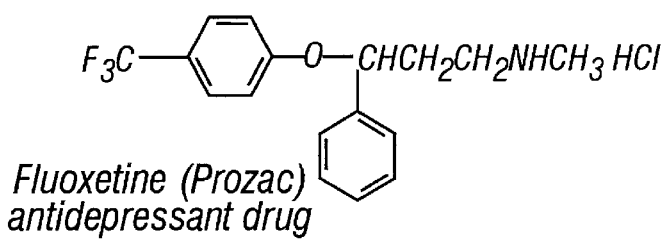
Fluoxetine (Prozac) antidepressant drug
FIG. 10

METHOD AND APPARATUS FOR DETERMINATION OF CARBON-HALOGEN COMPOUNDS AND APPLICATIONS THEREOF

CROSS REFERENCE TO RELATED APPLICATIONS

This application claims the benefit of U.S. Provisional Patent Application No. 60/091,090, filed Jun. 29, 1998; U.S. Provisional Patent Application No. 60/138,643, filed Jun. 10, 1999, and is a continuation of U.S. patent application Ser. No. 09/343,148, filed Jun. 29, 1999, now U.S. Pat. No. 6,307,625.

TECHNICAL FIELD

This invention relates generally to measuring and testing by dispersed light spectroscopy with Raman type light scattering, and more particularly to Raman spectroscopy for the determination of carbon-halogen and fluorooorganic compounds.

BACKGROUND

Qualitative and quantitative analysis of fluoroorganic compounds is an important practical task. Fluoroorganic compounds are widely used in the pharmaceutical industry. About one-third of all newly patented drugs contain carbon-fluorine (C—F) bonds. Examples of fluorine-containing drugs are the anticancer drug Fluoracil ($C_4H_3FN_2O_2$, 5-fluorouracil), antidepressant drug Prozac® ($C_{17}H_{18}F_3NO$, fluoroxetine) and painkiller Dalmane ($C_{21}H_{23}ClFN_3O$, flurazepam). Perflubron ($C_8F_{17}Br$, bromoperfluorooctane) is an oxygen-carrier in a formulation now undergoing clinical trials as a blood substitute. Many agricultural chemicals and pesticides also contain carbon-fluorine bonds.

Chemical analysis for drugs can be done by isolating the drug and then measuring concentrations of compounds. This approach can be expensive. Alternatively, known chemical compounds can be labeled with radioactive elements to form tracers. The radioactive compounds and their metabolites can be followed in the body or tissues by observing emitted radioactivity. However, making and disposing of radiolabeled compounds is also expensive. These expenses can be found in many drug development programs.

Accordingly, the inventors have determined that it would be useful to accurately and inexpensively identify fluoroorganic compounds. The present invention provides a method and apparatus for achieving this object.

SUMMARY OF THE INVENTION

The invention is directed to an apparatus and method for detecting the presence of compounds having carbon-halogen bonds using Raman spectroscopy. The method detects any carbon-halogen bond, and is particularly useful in detecting carbon-fluorine bonds.

In one aspect, the method uses pulsed laser Raman spectroscopy to detect carbon-halogen bonds, using an effect of inelastic scattering of light. A sample is irradiated from a noncontinuous periodic pulse light source, such as a metal-vapor laser. Raman scattered light emitted from the sample is then detected to determine if a characteristic Raman scattered light spectrum for a compound having a carbon-halogen is present in the sample.

In another aspect, the apparatus for Raman spectroscopy includes a noncontinuous periodic pulse metal vapor laser and a monochromator for visible and ultraviolet light. The apparatus also includes a detector for detecting the emitted Raman scattered light and a pulse recording system to eliminate primary fluorescence associated with the sample.

In yet another aspect, the invention is directed to a method for detecting a fluoroorganic compound that includes exposing a sample to an excitation light source and measuring a frequency of an acoustic mode of the compound. The method also includes measuring a frequency of an optical mode of the compound and detecting a shift in the optical and acoustic mode frequencies. The molecular length of the compound is approximated as a function of the shift in frequencies to determine the presence of the fluoroorganic compound.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 9 shows structures of some commercially useful fluoroorganic compounds.

FIG. 10 shows structures of various compounds having Raman spectra.

Like reference numbers and designations in the various drawings indicate like elements.

DETAILED DESCRIPTION

Figure 1:
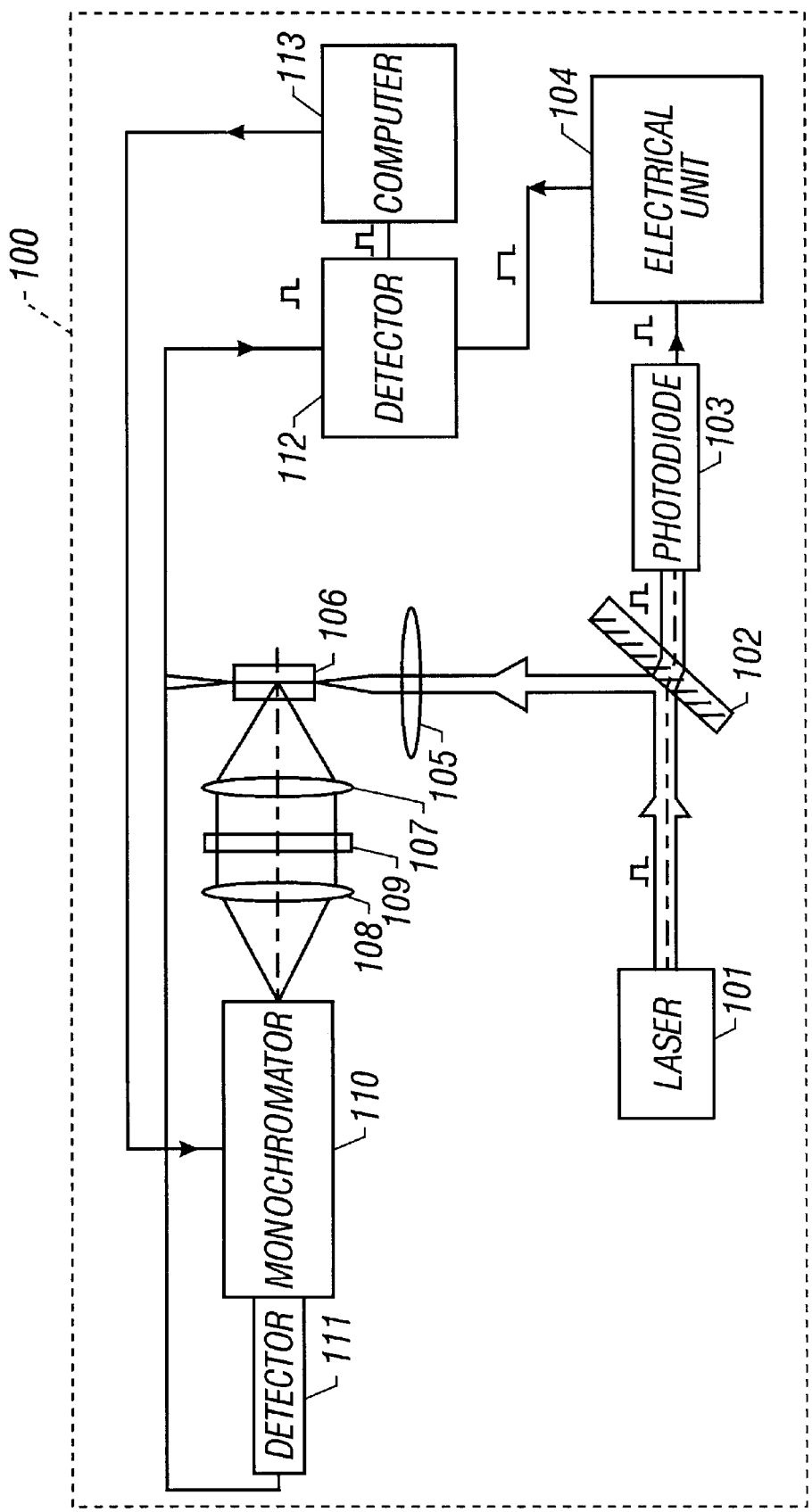
FIG. 1 is a schematic drawing of a Raman spectrometer in accordance with a preferred embodiment.

In general, the invention is directed to a method and an apparatus for determining the presence, in a sample, of compounds having carbon-halogen bonds and, in particular, carbon-fluorine bonds. The method uses pulsed laser Raman spectroscopy to detect carbon-halogen bonds, using an effect of inelastic scattering of light. The apparatus includes a metal-vapor laser source and a pulse recording system, to permit the recording of Raman signals for carbon-halogen bonds.

The invention is based on a principle different from most organic chemistry analyses, i.e., analysis by bond rather than analysis by compound. The method of the invention does not identify a compound; rather the presence of a carbon-halogen bond is determined, using the carbon-halogen bond as a chemical tracer. In particular, the method detects all types of carbon-fluorine bonds.

The method is useful for analysis of fluoroorganic compounds at $10^{-3}$–$10^{-6}$ g/L (ppm-ppb level) for pharmaceutical, biological, medical and biomedical applications, and for environmental analysis of water, soils and air contaminated with such compounds. Full development of resonance Raman technology may lead to detection at better than parts per billion levels. The invention usefully reduces the operational costs for analysis of fluoroorganic compounds (being less expensive than current methods based on extraction and compound isolation, with identification by chromatography or mass spectrometry), and makes such analysis more rapid.

The apparatus of the invention has several advantages for the observation of the Raman spectra of fluoroorganic compound. A periodic pulse vapor-metal laser source, such as copper-vapor or gold-vapor lasers, is used for sample excitation. Metal-vapor lasers are characterized by an ability to produce short and powerful pulses in the visible and ultraviolet region. These lasers are able to produce pulses of light with high peak and average operating power with air cooling.

Analysis for a carbon-fluorine bond rather than for a fluoroorganic compound specifically is possible because organic fluorine compounds with a carbon-fluorine bond are rarely not found in nature. Except for a few rare exceptional compounds found in a few plants or microorganisms (e.g., sodium fluoroacetate and fluorooleic acid, both found in certain plants in Africa), carbon-fluorine bonds generally do not exist in natural products (Key et al., *Environmental Science and Technology* 31: 2445–2454, 1997). Consequently, finding a carbon-fluorine bond in any system means an artificial compound exists in the sample. Additionally, all known biologically produced fluorinated organic molecules contain only one fluorine atom. If a fluorinated compound is found in or found on biologically derived animal or vegetable material, the compound is almost certainly artificial, not natural. If a fluorinated compound is injected or ingested by a vegetable or animal biological material, any fluoroorganic compound found must be the material injected or ingested or be a metabolite of the material injected or ingested. The carbon-fluorine bond is strong and generally cannot be modified biologically. This means that the carbon-fluorine bond can be used as a tracer group because the bond does not alter state when exposed to biological processes.

Unless otherwise defined, all technical and scientific terms used herein have substantially the same meaning as commonly understood by one of ordinary skill in the art to which this invention belongs. Although many methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present application, including definitions, will control. In addition, the materials, methods, and examples described herein are illustrative only and not intended to be limiting.

Other features and advantages of the invention will be apparent from the following detailed description, the drawings, and from the claims.

Raman Spectroscopy

An authoritative book (Wolverson, in *An Introduction to Laser Spectroscopy*, Andrews & Demidov, Eds., Plenum Press, New York, 1995, pp. 91–114) concisely defines Raman spectroscopy as follows: "Raman spectroscopy is the inelastic scattering of light by a material; the word 'inelastic' implies that energy is transferred between the light quanta and the material, so that the scattered light may have a longer or shorter wavelength than the incident light. The study of light scattered from a particular material is therefore termed Raman spectroscopy and is of interest because, as will be seen, information can be gained about the structure, the composition, and the vibrational or electronic states of the scattered material. Raman spectroscopy is a large field, with many variations on the basic technique and with many new applications being found each year." An older, alternative description of the Raman effect and Raman spectroscopy may be found in other sources, e.g., *Spectroscopy Source Book, Science Reference Series*, McGraw-Hill, New York, 1988, pp. 145–141.

The intensity of normal Raman peaks of the frequency of incident light is described by Skoog & Leary (*Principles of Instrumental Analysis*, $4^{th}$ edition, Saunders Publishing, Philadelphia, 1992, p. 301) as follows: "The intensity of power of a normal Raman peak depends in a complex way upon the polarizabiliy of the active group, as well as other factors. In the absence of absorption, the power of the Raman emission increases the fourth power of the frequency of the source; however, advantage can seldom be taken of this relationship because of the likelihood that ultraviolet radiation will cause photodecomposition. Raman intensities are usually directly proportional to the concentration of the active species. In this regard, Raman spectroscopy more closely resembles fluorescence than absorption, where the concentration-intensity relationship is logarithmic."

The teaching of the quoted authors bears importantly on the use of pulsed metal-vapor lasers. Conventional Raman spectroscopy using a continuous wave Nd:YAG laser does not have sufficient energy in the incident light to cause fluorescence. Because the intensity of the Raman signal is proportional to the fourth power of the frequency of incident light, and therefore inversely proportional to the fourth power of the wavelength of incident light, the signal strength of the inelastically scattered light is about 16 times greater at the wavelength of 510.6 nm (copper-vapor laser) than at the conventionally used wavelength of 1064 nm (Nd:YAG laser). Other lasers operating with higher energy continuous wave light (such as argon at 488.8 and 514.5 nm, krypton at 647.1 nm, and helium-neon at 632.8 nm) cause photodecomposition of samples, as described by Skoog & Leary, above. When any compound in a sample mixture gives primary fluorescence, then observation of Raman spectra of the sample is severely limited. In contrast, by using a pulsed laser at about 10,000 Hertz and a very short pulse width of about 12 nanoseconds, samples do not undergo the photo-decomposition discussed by Skoog & Leary, above. Using a pulsed copper-vapor laser permits elimination of inherent fluorescence by using a timing-gate for the detector. The invention thus uses higher energy incident light to give a much stronger signal.

Apparatus

The Pulsed Laser Raman Spectroscopy of the invention is achieved using non-continuous periodic pulse vapor metal laser sources and by using a stroboscopic pulse recording system. Suitable lasers include copper-vapor or gold-vapor lasers. Alternatively, any pulsing light source such as a solid state light source or a light bulb can be used. The apparatus can be a modification of copper-vapor and gold-vapor lasers that have been used to provide energy for two-photon excitation of a compound. (Gorelik et al., *Journal of Molecular Structure* 266: 121–126, 1992; Gorelik & Kozulin, *Quantum Electronics (Russia)* 21: 499–501, 1994; Gorelik & Zhabotinskii, *Quantum Electronics (Russia)* 24: 273–275, 1994). In Gorelik's two-photon excitation studies, exciting light was green (510.5 nm) or yellow (578.2 nm) from the copper-vapor laser or red (627.8 nm) from the gold-vapor laser. The goal of these studies was the production of primary fluorescence in the ultraviolet and blue ranges of the spectra. The above studies did not contemplate Raman spectroscopy of the carbon-fluorine bond. For Raman spectroscopy, efforts are made to eliminate primary fluorescence and to collect only the inelastically scattered Raman light. For resonance Raman spectroscopy, a frequency doubling crystal is required.

Metal-vapor lasers are air cooled or water cooled and consume only about 1–2 kW of electrical power. These lasers may have a coefficient of efficiency of about 1%. The air-cooled copper-vapor laser operates at an average power of about 1–10 watts. This means that metal vapor lasers operate more efficiently and cost less to operate than many other laboratory lasers. Thus, the laser can be combined with other commercial components to produce an inexpensive Raman instrument for obtaining Raman spectra of fluoroorganic compounds. A Raman instrument can be designed for spectral range of about 550–900 cm$^{-1}$. The instrument can also be designed for a range of about 500–1500 cm$^{-1}$. In this case, the instrument may be capable of presenting detection in the normal 1000–1400 cm$^{-1}$ vibrational range of the carbon-fluorine bond.

FIG. 1 illustrates a Raman instrument 100 that includes a metal-vapor laser. Suitable lasers include a copper-vapor or a gold-vapor laser. The Raman instrument 100 also includes a mirror 102 with dielectric and highly reflective coating to efficiently reflect a generated laser radiation, and a photodiode 103 for collecting a laser radiation. The instrument 100 also includes an electronic unit 104 (e.g., a stroboscopic generator) and a condensing lens 105 that focuses a laser beam on the sample 106 to be analyzed (the sample 106 not being a component of the apparatus). Condensing lenses 107 and 108 are used to focus beams on the spectrometer slit after passing through the sample 106 and an absorbance filter 109 is used to pass a Raman emission signal (secondary radiation). The Raman instrument 100 also includes a single or double monochromator spectrometer 110, a detector of secondary radiation 111 (e.g., a photomultiplier), a pulse recording system 112 controlled by the stroboscopic system 104, and, optionally, a computer 113 for data collection and processing and for management of the spectrometer 110. The spectrophotometer 110 may be a single, double, or triple monochomator for the visible and ultraviolet region of the spectra, equipped with a photomultiplier 111 and sensitive photon-counting detector system 112. The high energy laser 101 pulses irradiate the fluoroorganic sample 106 and also activate a device 104, to form a strobe-impulse used to synchronize the pulse recording system 112. Samples preferably are placed into cylindrical quartz cuvettes having parallel windows (not shown). Raman spectra is observed at 90° with respect to the incident pulse by using a single or double monochromator 110 with a single channel detection. When irradiated, the sample 106 emits pulsed Raman radiation and also scatters part of the incident Raman pulse. The absorbance filter 109 removes scattered radiation and passes the pulsed Raman radiation to the spectrometer 110. Signals are photomultiplied and sent to a synchronized pulse recording system 112. To obtain ultraviolet radiation (255.3 nm; 271.2 nm and 289.1 nm), a doubling crystal, such as $BaB_2O_4$, or a tripling crystal, can be used.

A suitable laser 101 that can be used with the apparatus is designed and manufactured at Lebedev Institute of Physics (Russian Academy of Sciences, Moscow, Russia). One such laser is a 3-watt or 10-watt Russian-designed air-cooled copper-vapor laser manufactured by the Lebedev Physics Institute. A stroboscopic generator 104 that can be used with the instrument 100 is also designed and manufactured at Lebedev Institute of Physics (Russian Academy of Sciences, Moscow, Russia). The spectrophotometer 110 can be any standard monochomator or a commercial product such as a Jobin-Yvon U1000 double monochromator Raman spectrometer. Preferably, this spectrophotometer is modified to permit observation of the spectra of fluoroorganic compounds as shown in FIGS. 2–8, below. The optical filter can be a GUI-6 absorption optical filter. The monochromator can be an MSD-2 monochromator. The photomultiplier 111 can be an FEU-106 photomultiplier.

Excitation light emitted by the metal-vapor laser 101 are attenuated by an optical absorption filter 109 placed in front of a sample 106. The filter 106 is used to limit the excitation light going to the sample. In the spectral range 200–400 nm, the filter 109 can be an ultraviolet filter, such as a GUI-6. In the range 360–480 nm, the filter can be a blue wavelength filter, such as a BG-12. GUI-6 and BG-12 filters are commercially available from AGFA. The luminescence spectra are preferably normalized to allow for the transmission coefficient of the relevant filter 109.

A pulsed metal-vapor laser 101 has significant advantages over continuous wave argon or helium-neon lasers. The pulsed signal generates significantly less photodecomposition and permits the simple elimination of primary fluorescence, as described by Skoog & Leary, above. Further, laser 101 is significantly cheaper than Raman spectrometers that use longer wavelength excitation lasers, particularly to the Nd:YAG laser at 1064 nm, to eliminate fluorescence. This is because the longer wavelength lasers require expensive CCD signal detectors that significantly increase cost.

The metal-vapor laser 101 can provide about 16 times the signal of commercial Nd:YAG laser Raman spectrometers. Because the Raman vibrational scattering emissions are detected during a narrow time internal ("gate") approximately equal to the laser pulse duration ($10^{-8}$ sec), fluorescence is eliminated. Pulsed techniques also give enhanced sensitivity.

Thus, the intense characteristic Raman band of the symmetric vibrational normal mode of carbon-fluorine bond or groups in the Raman spectra of organic compounds, excited by the pulse laser source, can be established. For example, to achieve optimal excitation of a C—F band, the exposure of the sample to the excitation source must be $10^{-8}$ seconds or more. Preferably, the Raman spectrum is measured within the above exposure period. Therefore, the Raman spectra is not affected by fluorescence.

The present inventors have discovered that, using the Raman instrument 100, an emitting signal of a carbon-fluorine bond normal mode (vibrational) or carbon-fluorine group normal mode (rotational), which occurs within a narrow frequency range, is very strong with recognizable narrow band widths. The term "normal mode" refers to the symmetric vibrational process of excited atoms. The radiation characteristic of carbon-fluorine bonds may be detected in the 500–800 $cm^{-1}$ region. Other radiation in the 950–1400 $cm^{-1}$ region commonly associated with fluoroorganic compounds can also be observed.

The published frequency range for carbon-fluorine bond infrared absorption is 1000 $cm^{-1}$ to 1400 $cm^{-1}$. These other bands are useful and can be used to confirm carbon-fluorine groups detected by the method of the invention. However, these infrared absorptions are subject to interference by other functional groups in the fluoroorganic compound, as discussed above.

A type of carbon-fluorine bond can also be identified in the preferred method. It is contemplated that the method of the invention does not measure the vibration of fluorine against carbon (such C—F vibrations occur in the infrared at 1000–1400 $cm^{-1}$). Rather, the method detects deviations from the totally symmetric Raman active mode of the groups (such as the carbon-fluorine group in the aromatic compound hexafluorobenzene or the trifluoromethyl group in trifluoromethylated compounds, such as 1,3,5-tris (trisfluoromethyl)benzene). The method detects changes in the polarization of carbon-fluorine groups as part of the total molecular vibrational normal modes.

The laser 101 is adaptable to frequency doubling to give a strong signal in the ultraviolet (UV) at about 255.4 nm. UV signals at 272 nm and 289 nm are also available. Irradiation of samples in the ultraviolet allows the observation of resonance Raman spectra which have signals approximately $10^4$ to $10^5$ stronger (10,000–100,000 times stronger) than normal Raman signals. Resonance Raman signals means detection of compounds containing carbon-fluorine bonds at the parts per billion (ppb) level. Frequency doubling of the wavelengths is observed for both the copper-vapor laser and the gold-vapor laser.

Figure 6:
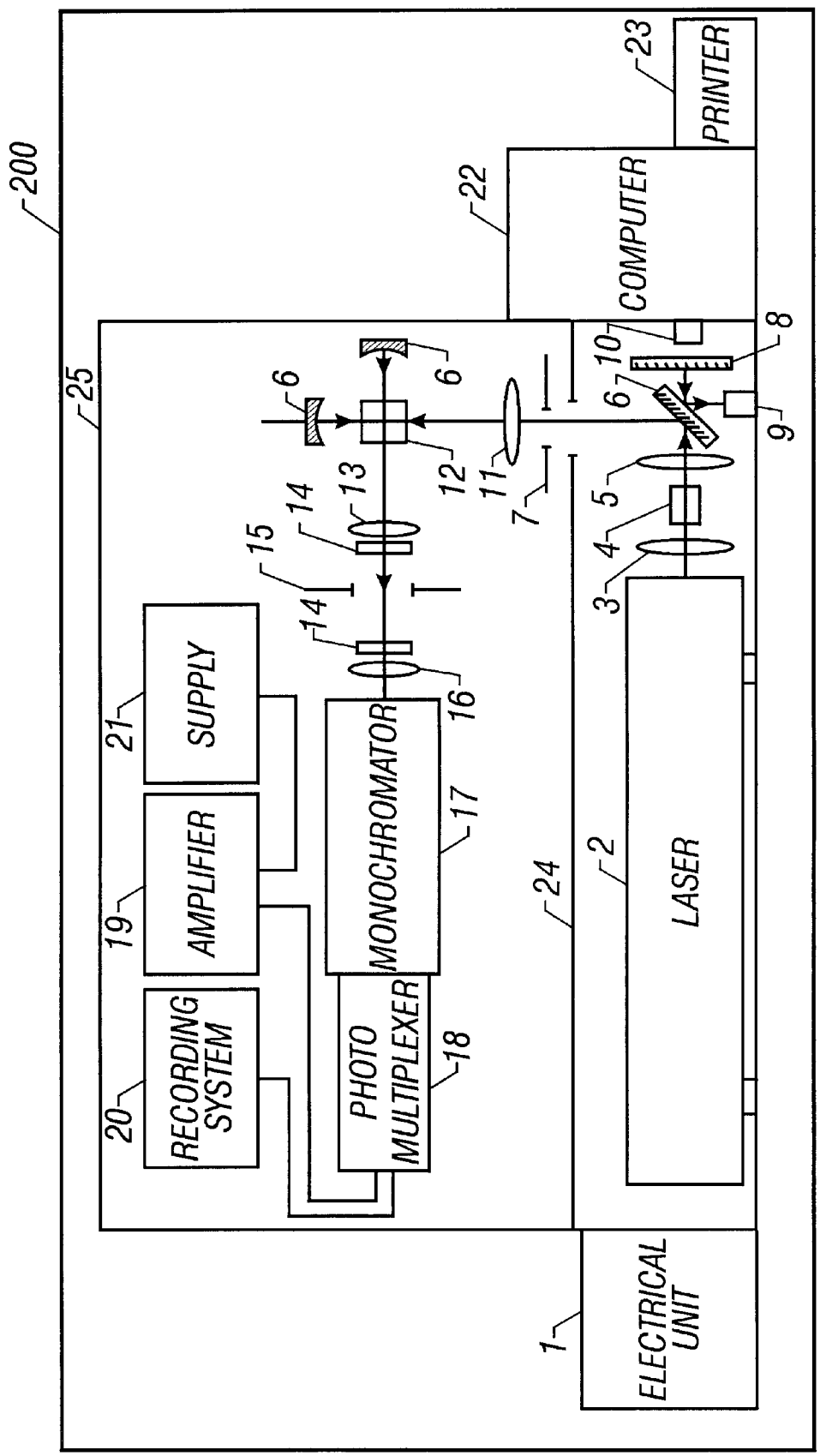
FIG. 6 is a schematic drawing of a resonance Raman spectrometer in accordance with a preferred embodiment.

FIG. 6 is a schematic drawing of a Raman spectrometer 200 as adapted for resonance Raman spectroscopy. The Raman spectrometer 200 is similar to the Raman instrument 100 in FIG. 1. However, the spectrometer 200 includes a non-linear frequency doubling crystal 4. The frequency doubling crystal can be constructed of barium borate. The spectrometer 200 may also include additional filters 14.

The doubled frequencies, expressed as wavelengths, for a copper-vapor laser may be about 255 nm and 289 nm. A combination band at 272 nm may also be useful. For a gold-vapor laser, the doubled frequency wavelength is about 314 nm. Almost all of the compounds of TABLE 1 below have aromatic rings and are almost certain to give significant enhancement of the resonance Raman emission signal due to the high self-absorbance of the aromatic ring structures. Aromatic rings absorb energy at frequencies similar to those emitted (self-absorption). Using a frequency doubling crystal, the frequency may be shifted from 510.6 nm to 255.3 nm where it is absorbed.

The spectrometer 200 permits a significant suppression of dark current and environmental noise, and also increases sensitivity. The background of continuous fluorescence can be suppressed by using a strobe-impulse. The strobe-impulse is synchronized with a laser source pulse and "opens" a detection system for only about $10^{-8}$ sec. This period corresponds to the duration of the preferred laser pulse. As a result, the spectrometer 200 permits a low level detection of fluoroorganic compounds.

Compounds

A Raman band that is characteristic of carbon-fluorine bonds can be found in the range 540 $cm^{-1}$ to 785 $cm^{-1}$, based on experimental observations. For estimation purposes, a range of 500–800 $cm^{-1}$ is reasonable.

Many fluoroorganic compounds are manufactured commercially. Most of the compounds find use as drugs in medicine or veterinary medicine, anesthetics, herbicides, insecticides, pesticides or as industrial intermediates. FIG. 9 shows the structures of some commercially useful compounds. These compounds include carbon-fluorine bonds of trifluoromethyl groups, aromatic carbon-fluorine bonds, and perfluoroalkyl groups.

Aromatic carbon-fluorine bonds are observed in the range of 540–610 $cm^{-1}$. Examples are hexafluorobenzene, 569 $cm^{-1}$; and pentafluoropyridine, 589 $cm^{-1}$.

Figure 5:
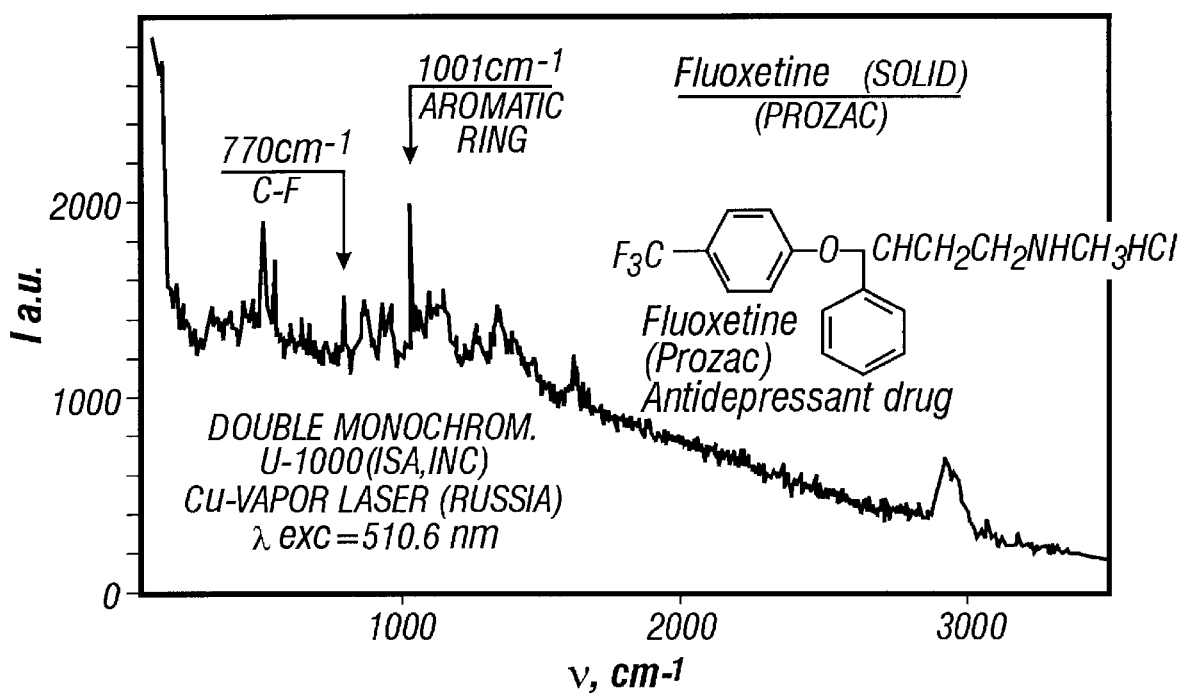
FIG. 5 is a Raman spectrum of a commercial preparation of fluoxetine hydrochloride using the spectrometer of FIG. 1.

Trifluoromethyl groups are observed in the range of 710–785 $cm^{-1}$. Examples are: 1-bromoperfluorooctane, 726 $cm^{-1}$; perfluorodecanoic acid, 730 $cm^{-1}$; triperfluoropropylamine, 750 $cm^{-1}$; 1,3,5-tris-(trifluoromethylbenzene), 730 $cm^{-1}$; fluoxetine (Prozac®) commercial powdered pill at 770 $cm^{-1}$. TABLE 1 (see, Key el al., *Environmental Science and Technology* 31: 2445–2454, 1997) lists commercial fluoroorganic compounds containing trifluoromethyl groups. Most of these compounds have an aromatic ring, so resonance Raman can be observed. For example, Prozac® gives a sharp identifiable signal at 770 $cm^{-1}$, as shown in FIG. 5.

TABLE 1

| APPLICATIONS OF TRIFLUOROMETHYL-SUBSTITUTED ORGANIC COMPOUNDS | | | | |
|---|---|---|---|---|
| Herbicides | Herbicides | Insecticides | Fungicide | Medicinal (Use) |
| acifluorifen | flurtamone | acrinathrin | fluazinam | bendroflumethiazide |
| benfluralin | fluxofenim | bifenthrin | flusulfamide | (antihypertensive) |
| diflufenican | fomesafen | chlorfluazuron | flutolanil | dexfenfluramine |
| dinitramine | furyloxyfen | cyhalothrin | furconazole | (obesity) |
| dithiopyr | haloxyfop | flucofuron | triflumizole | fenfluramine |
| ethaifluralin | lactofen | flufenoxuron | Anaesthetics | (anorectic) |
| flazasulfuron | mefluidide | X-fluvalinate | fluroxene | fluoxetine |

TABLE 1-continued

APPLICATIONS OF TRIFLUOROMETHYL-SUBSTITUTED ORGANIC COMPOUNDS

| | | | | |
|---|---|---|---|---|
| fluazifop | nipyraclofen | hydramethylnon | halothane | (antidepressant) |
| fluchioralin | norflurazon | tefluthrin | methoxyflurane | fluphenazine |
| flumetralin | oxyfluorfen | triflumuron | isoflurane | (antipsychotic) |
| fluometuron | perfluidone | Rodenticide | sevoflurane | halofantrine and |
| fluoroglycofen | prodiamine | bromethalin | desflurane | mefloquine.HCl |
| flurazole | profluralin | flocoumafen | Lampricide | (antimalarials) |
| flurochloridane | thiazafluron | flupropadine | trifluoromethyl- | nilutamide (cancer) |
| flurprimidol | trifluralin | | nitrophenol | tolrestat (diabetes) |

When no trifluoromethyl group is present, difluoromethylene groups are observed in a range centered at 690 cm$^{-1}$. An example is perfluorodecalin, a component of blood substitutes developed in Japan and Russia.

In particular embodiments, Raman spectroscopy can be performed on 1-bromoperfluorooctane ($C_8F_{17}Br$; BPFO), polycrystalline perfluorodecanoic acid ($C_9F_{19}COOH$; PFDA), 1,3,5-tris-(trifluoromethyl)-benzene ($C_6H_3(CF_3)_3$; TTFMB); or fluoxetine (Prozac®). The first compound ($C_8F_{17}Br$) is a candidate to carry oxygen in a blood substitute. The second compound ($C_8F_{17}COOH$) is an analog of perfluorooctanoic acid (PFOA), but less volatile. PFOA has been found in tissues of workers exposed to PFOA in the workplace. The third compound ($C_6H_3(CF_3)_3$) contains carbon-fluorine bonds that are in trifluoromethyl groups. $C_6H_3(CF_3)_3$ is an analog of many useful compounds now sold commercially as drugs, herbicides, and pesticides, some of which are presented in TABLE 1. Fluoxetine (Prozac®; $C_{17}H_{18}F_3NO$) is a widely prescribed drug which contains a trifluoromethyl group.

In further embodiments, resonance Raman spectroscopy can be performed on perfluorodecalin ($C_8F_{18}$, PFD) and 1-bromoperfluorooctane ($C_8F_{17}Br$, BPFO). The schematic of the instrument used to observe the resonance Raman spectra is given in FIG. 6. Most of the compounds of TABLE 1 should give enhanced resonance Raman spectra.

Figure 2:
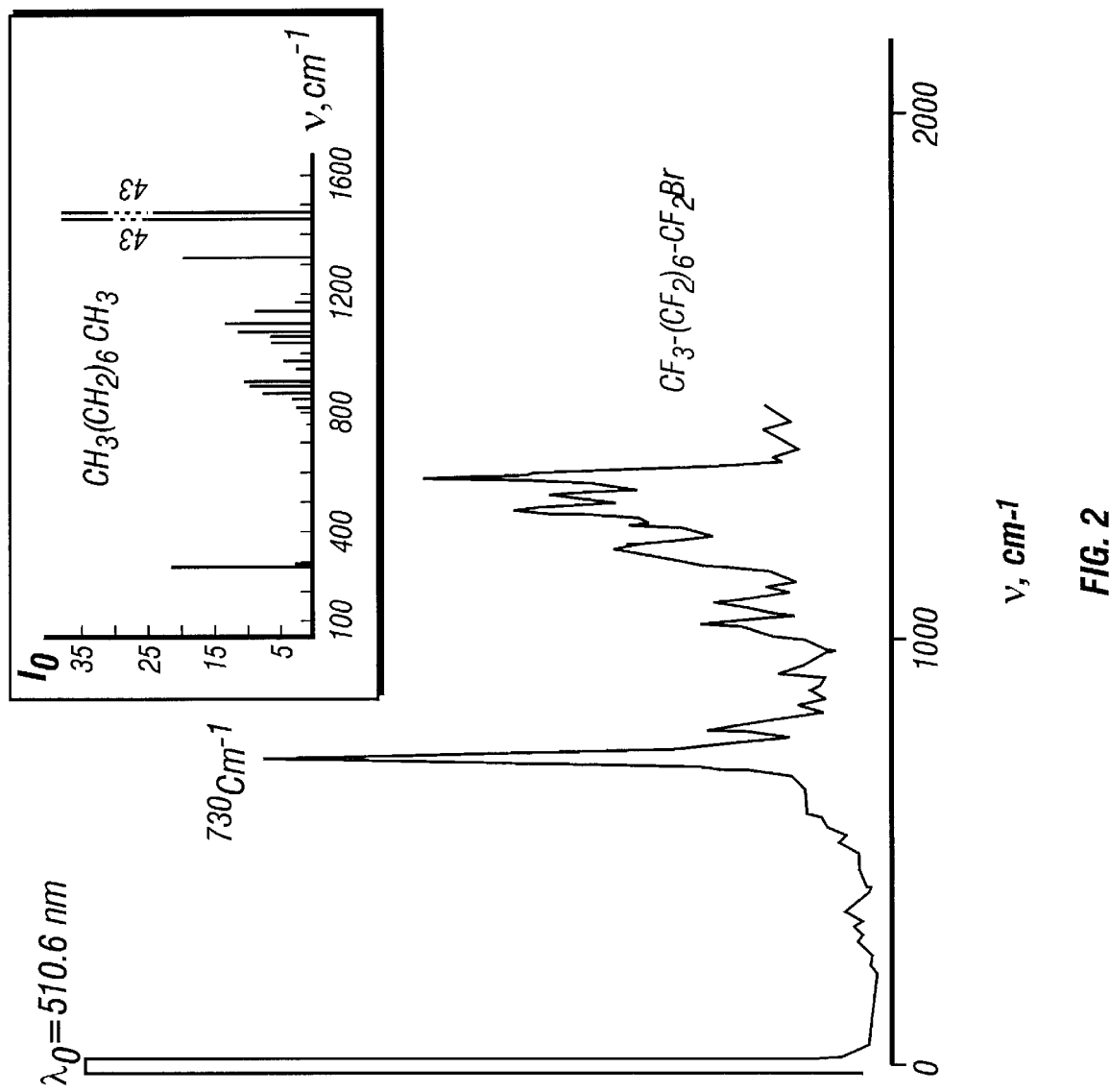
FIG. 2 is a Raman spectrum of $C_8H_{17}Br$ (bromoperfluorooctane) and $C_8H_{18}$ using the spectrometer of FIG. 1.

A Raman spectrum (0–1500 cm$^{-1}$) of liquid $C_8F_{17}Br$ (BPFO) is shown in FIG. 2. A very strong peak at 730 cm$^{-1}$ is present in this spectrum. The compound $C_8F_{17}Br$ is a fluoro-derivative of octane ($C_8H_{18}$) in which the 18 hydrogens are replaced with 17 fluorine atoms and one atom of bromine. FIG. 2 also shows a Raman spectrum of $C_8H_{18}$ in the upper right corner. This spectrum does not have a peak near 730 cm$^{-1}$. As in $C_6H_3(CF_3)_3$ spectrum, the appearance of the 730 cm$^{-1}$ peak in $C_8F_{17}Br$ is due to a carbon-fluorine bond signature. This peak corresponds to a fully symmetric vibrational normal mode of a molecule containing the carbon-fluorine bond, specifically the trifluoromethyl group or perfluoroalkyl group.

Figure 3:
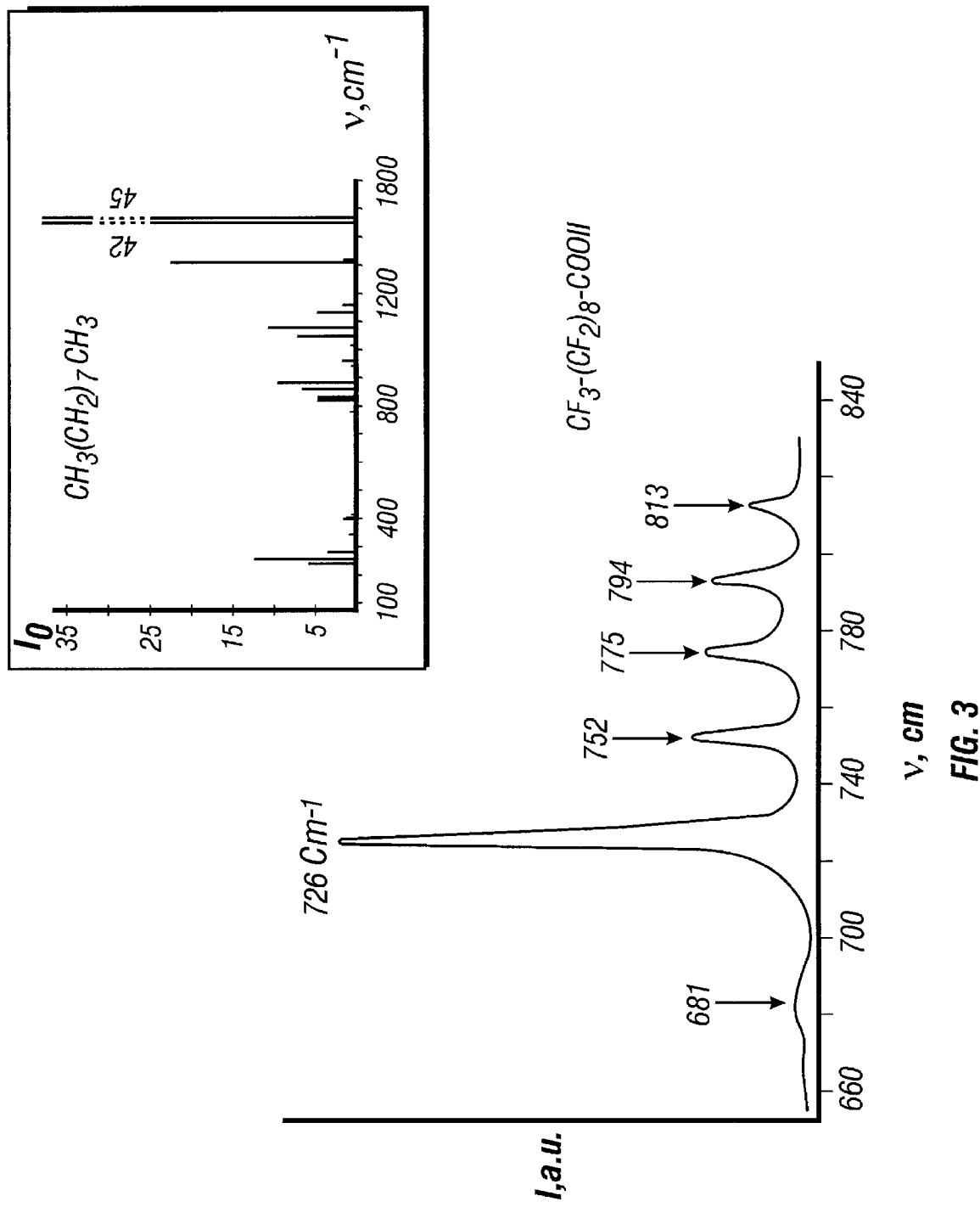
FIG. 3 is a Raman spectrum of $C_9F_{19}COOH(C_{10}HF_{19}O_2$; bromoperfluordecanoic acid). $C_9H_{20}$ (nonane, a hydrocarbon) using the spectrometer of FIG. 1.

A Raman spectrum for polycrystalline $C_9F_{19}COOH$ (PFDA) is given in FIG. 3. As for earlier discussed fluoroorganic compounds, a characteristic peak at 726 cm$^{-1}$ has been observed for $C_8F_{17}COOH$. This peak was assigned as a fully symmetric vibrational normal mode of a molecule containing the C—F bond, specifically the trifluoromethyl group or perfluoroalkyl group. The Raman spectrum of nonane ($C_9H_{20}$) is shown in the upper right corner in FIG. 3. The nonane spectrum does not have any characteristic spectral lines close to 730 cm$^{-1}$.

Figure 4:
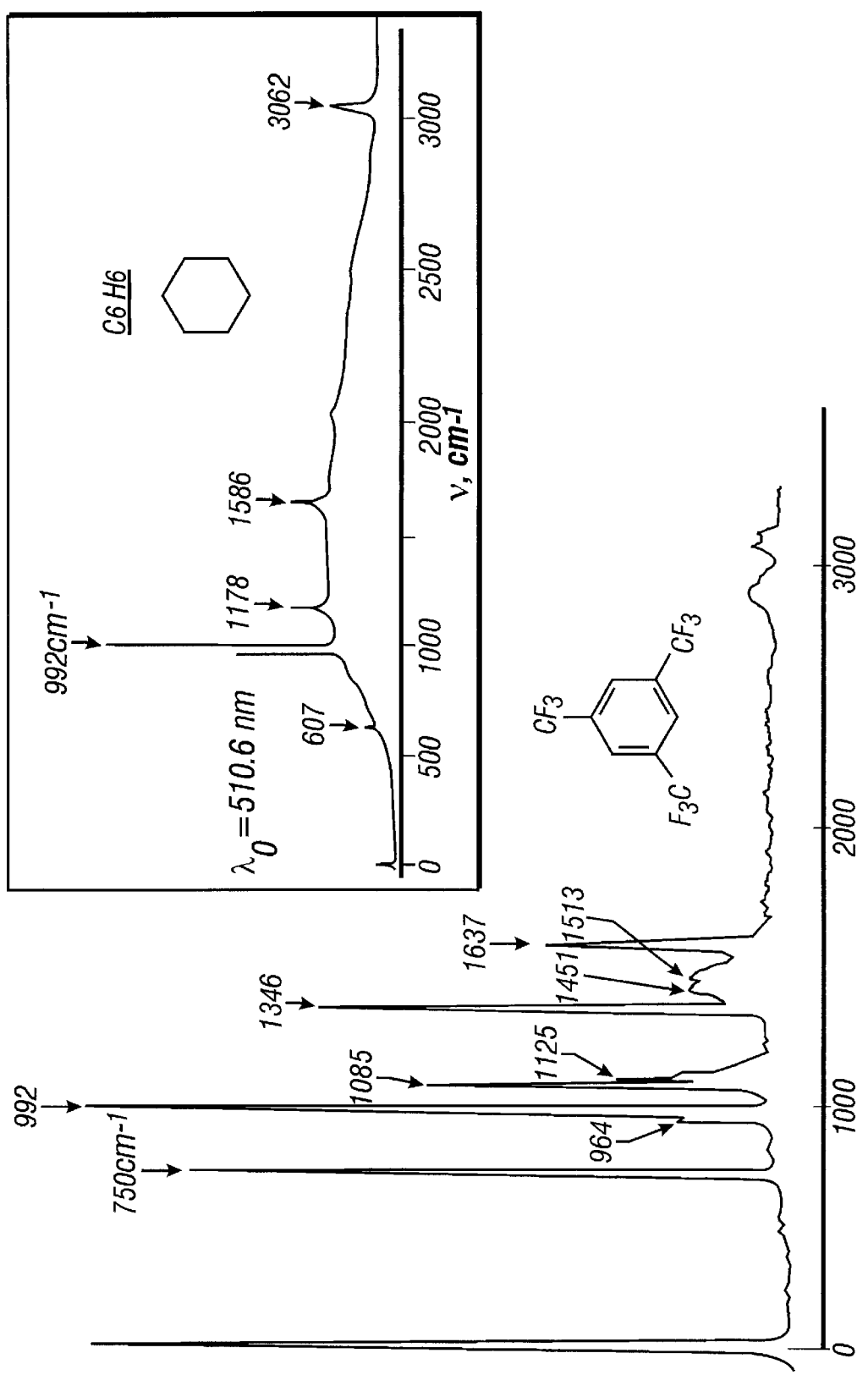
FIG. 4 is a Raman spectrum of $C_6H_3(CF_3)_3$ [1,3,5-tris(trisfluoromethyl)benzene] and $C_6H_6$ (benzene) using the spectrometer of FIG. 1.

A Raman spectrum for $C_6H_3(CF_3)_3$ (TTFMB) and benzene ($C_6H_6$, upper right) are shown in FIG. 4. When these two Raman spectra are compared, each has a well-resolved peak at 992 cm$^{-1}$, which corresponds to the fully symmetric vibrational mode of the benzene ring. At wave numbers greater than 992 cm$^{-1}$ the Raman spectrum of $C_6H_3(CF_3)_3$ shows a doublet at 1085$^{-1}$, 125 cm$^{-1}$, and spectral lines at 1376 cm$^{-1}$, 1513 cm$^{-1}$, and 1637 cm$^{-1}$ instead of the single lines at 1178 cm$^{-1}$ and 1586 cm$^{-1}$ found for carbon in benzene. The difference between $C_6H_3(CF_3)_3$ and unsubstituted benzene becomes apparent below 992 cm$^{-1}$. Benzene shows only two weak peaks which correspond to the deformation modes of the C—C bond. By contrast, $C_6H_3(CF_3)_3$ shows a strong peak at 730 cm$^{-1}$ comparable in intensity to the peaks in $C_6H_3(CF_3)_3$ and $C_6H_6$ at 992 cm$^{-1}$. The 730 cm$^{-1}$ peak is assigned as a fully symmetric vibrational normal mode of the trifluoromethyl group of the molecule.

The Raman spectrum in FIG. 5 is of the contents of a fluoroxetine ($C_{17}H_{18}F_3NO$) hydrochloride (Prozac®) capsule in the solid powdered form. The composition of the capsule is unknown other than the presence of fluoroxetine hydrochloride. The very narrow sharp peak at 770 cm$^{-1}$ is assigned to a symmetrical vibration involving the trifluoromethyl group. The symmetric aromatic vibration is found at 1001 cm$^{-1}$.

The Raman spectra of each of the four fluoroorganic compounds ($C_8F_{17}Br$, $C_8F_{17}COOH$, $C_6H_3(CF_3)_3$, and $C_{17}H_{18}F_3NO$) show a characteristic fully symmetric vibrational strong peak at frequencies in the range of 720–770 cm$^{-1}$ which are assigned to molecular vibrations of the trifluoromethyl group or perfluoroalkyl groups. Comparison of the Raman spectra of the fluoroorganic compounds with their hydrocarbon analogs, suggest that the observed spectral emissions in the range of 690–770 cm$^{-1}$ are associated with the carbon-fluorine bonds of the compounds studied.

Figure 7A:
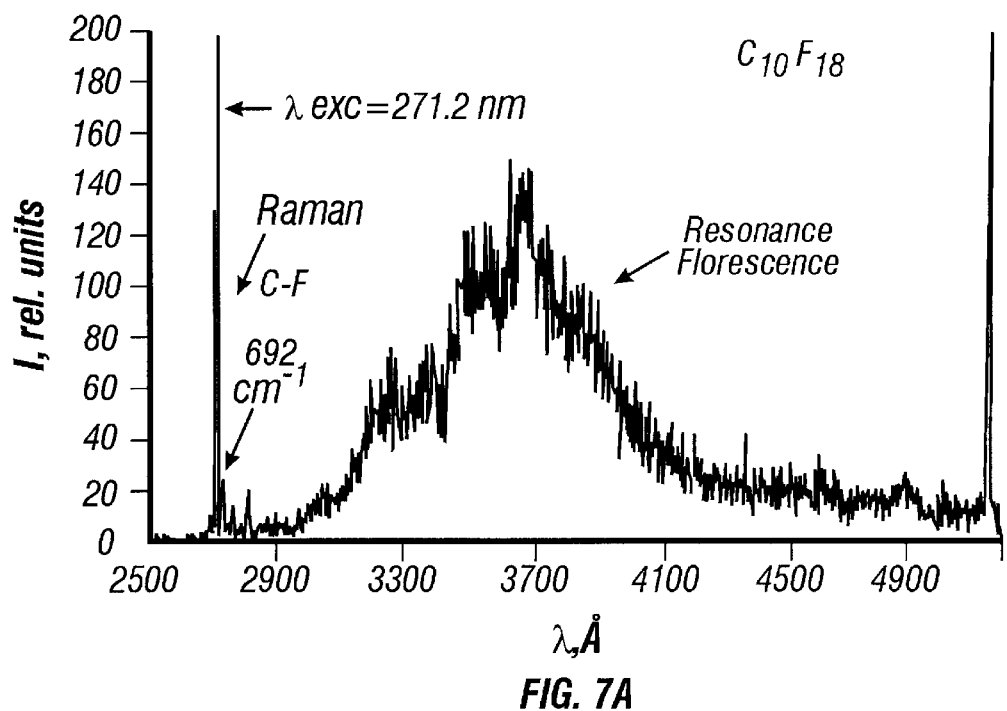
FIG. 7 is a resonance Raman spectrum of irradiate perfluorodecalin showing a difluoromethylene absorption. The top spectrum is an unprocessed resonance Raman spectrum of perfluorodecalin ($C_{10}F_{18}$). The bottom spectrum is a partially processed resonance Raman spectrum of perfluorodecalin.
Figure 7B:
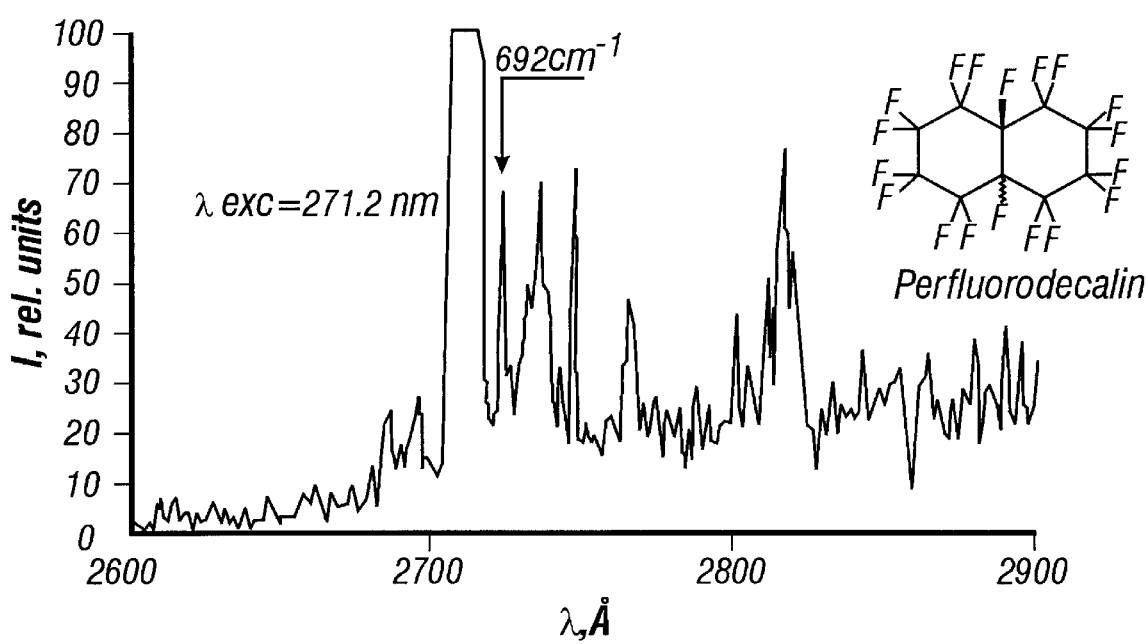
Figure 8:
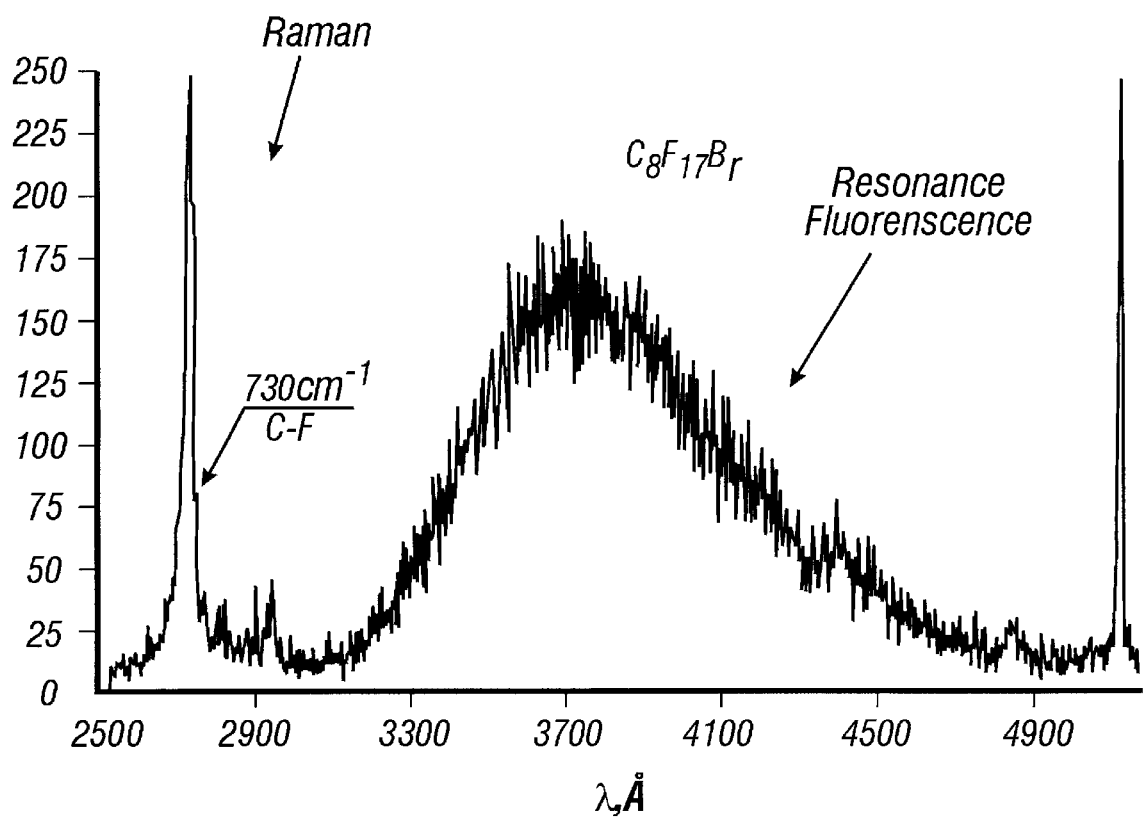
FIG. 8 is a resonance Raman spectrum of 1-bromoperfluorooctane using the spectrometer of FIG. 6.

Resonance Raman spectra of perfluorodecalin ($C_8F_{18}$) and 1-bromofluorooctane ($C_8F_{17}Br$) are shown in FIG. 7 and FIG. 8. These spectra are shown at two different scales, but are not otherwise electronically processed to enhance the signals. The narrow sharp emission at 692 cm$^{31\ 1}$ is believed to be the totally symmetric normal mode of the difluoromethylene groups ($CF_2$). 1-bromoperfluorooctane has a weak ultraviolet absorption maximum about 275 nm ($\in$=50) and gives a resonance Raman spectrum with a 730 cm$^{-1}$ emission signal, which is the same emission shown in the regular Raman spectrum (FIG. 2).

Quasi-one-dimensional molecules

As described above, the preferred method detects compounds having carbon-fluorine bonds. It has also been found that carbons in the "quasi-linear" or "quasi-one-dimensional" fluororganic molecule chain having a formula $C_nH_{2n+2}$ e.g., $C_nF_{2n+1}$ can also be identified. These molecules are often used in drug formulations, which transport oxygen or carbon dioxide in blood substitutes. These molecules are also used in other pharmaceutical and medicinal applications. Examples of these molecules include $C_{11}H_{11}F_3N_2O_2$ (flutamide) and $C_{10}F_{19}O_2K$ (potassium perfluorodecanoate).

Many linear or quasi-linear fluororganic compounds with different substitution groups can be identified. For example, a substitution group occurs when hydrogens of a molecule are replaced with fluorine to create a fluorocarbon compound. Suitable compounds include anesthetics and those listed in Table 2 below.

The $C_nH_{2n+2}$ molecules may be modeled as a resonator. The length of the molecule is inversely proportional to the number of carbons ("n") in the hydrocarbon chain, if n is relatively large. The present inventors have discovered that the fluororganic compounds experience a longitudinal acoustic mode (LAM) and a longitudinal optical mode (LOM) frequency shift. These shifts are dependent on the number of carbons in the molecule chain.

A Raman spectra was obtained using an argon laser at about 488.0 nm or a copper-vapor laser at about 510.5 nm. The laser power was about 100 mW. A computerized DFC-24 recording spectrometer with 1 cm$^{-1}$ slit width was employed which was capable of monitoring the position of the gratings. The samples were clear liquid or white crystalline powders. Quartz cuvettes with parallel windows and close fitting tops were used for liquid samples. Raman observations were made at 90-degrees from the incident radiation.

Figure 11:
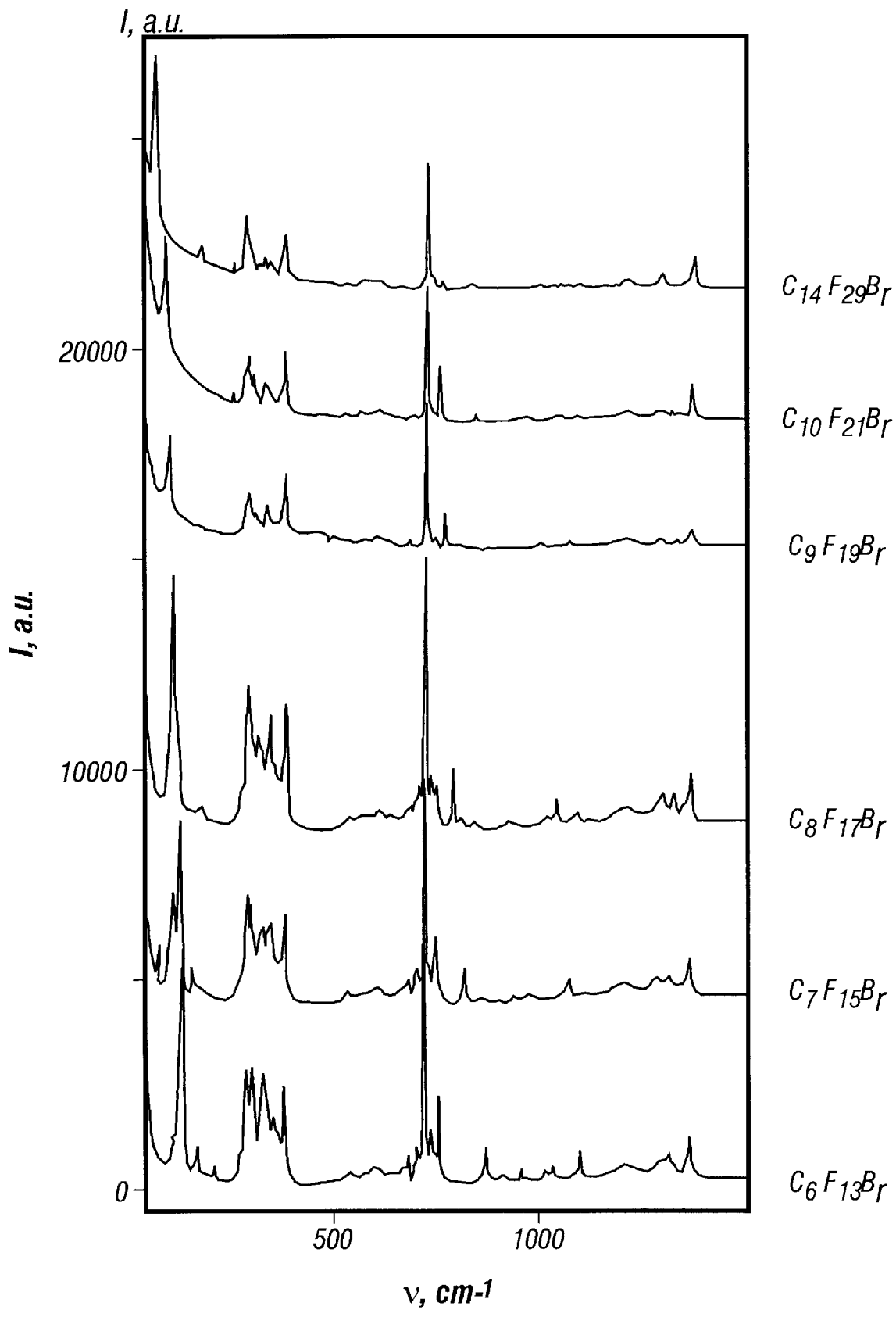
FIG. 11 illustrates Raman spectra of $C_nF_{2n+1}Br$ for n=6, 7, 8, 9, 10, 14 in the region 0–1500 cm$^{-1}$.
Figure 12:
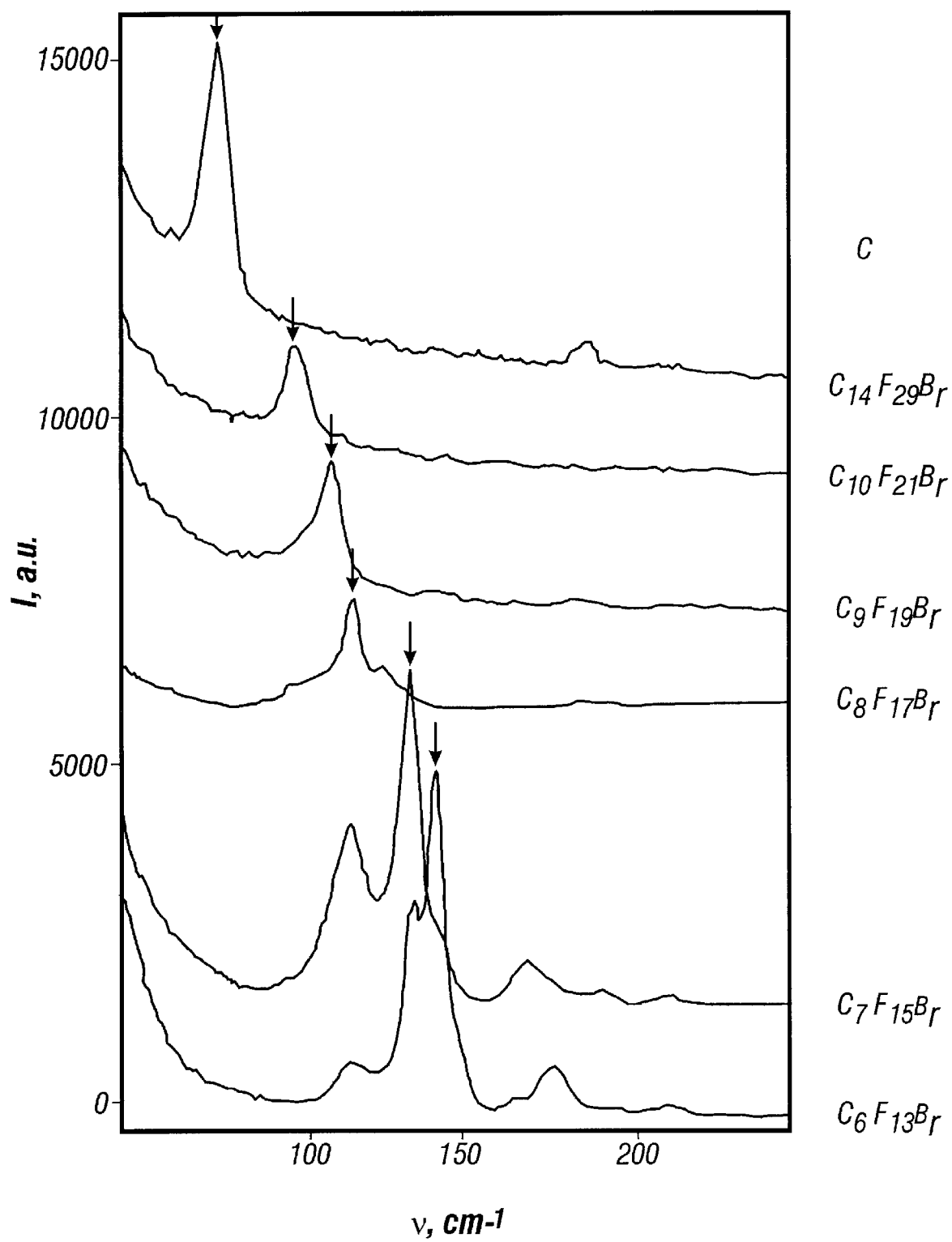
FIG. 12 illustrates the dependency of Raman spectra on the unit length of a molecule in the lower frequency region LAM.

FIG. 11 shows Raman spectra in the region 0–1400 cm$^{-1}$ for $C_nF_{2n+1}Br$. A sharp peak in the region 719–730 cm$^{-1}$ was observed for all Raman spectra. This peak corresponds to the fully symmetrical normal vibration of $CF_2$ bond. FIG. 12 illustrates that with an increase in n, the maximum peak increased linearly. This means that the peak intensity depends on the length of the molecule.

FIG. 12 illustrates an intensive peak in the region 0–500 cm$^{-1}$ and overlapping bands in the region 200–300 cm$^{-1}$. For n=6, 7, and 8, the observed lower frequency band (LAM) included several components. For n=9, 10 and 14 the band did not have splitting. A peak signal that was single was observed from $C_{14}$ to $C_9$. However, from $C_8$ to $C_6$, the peak began to split.

Figure 13:
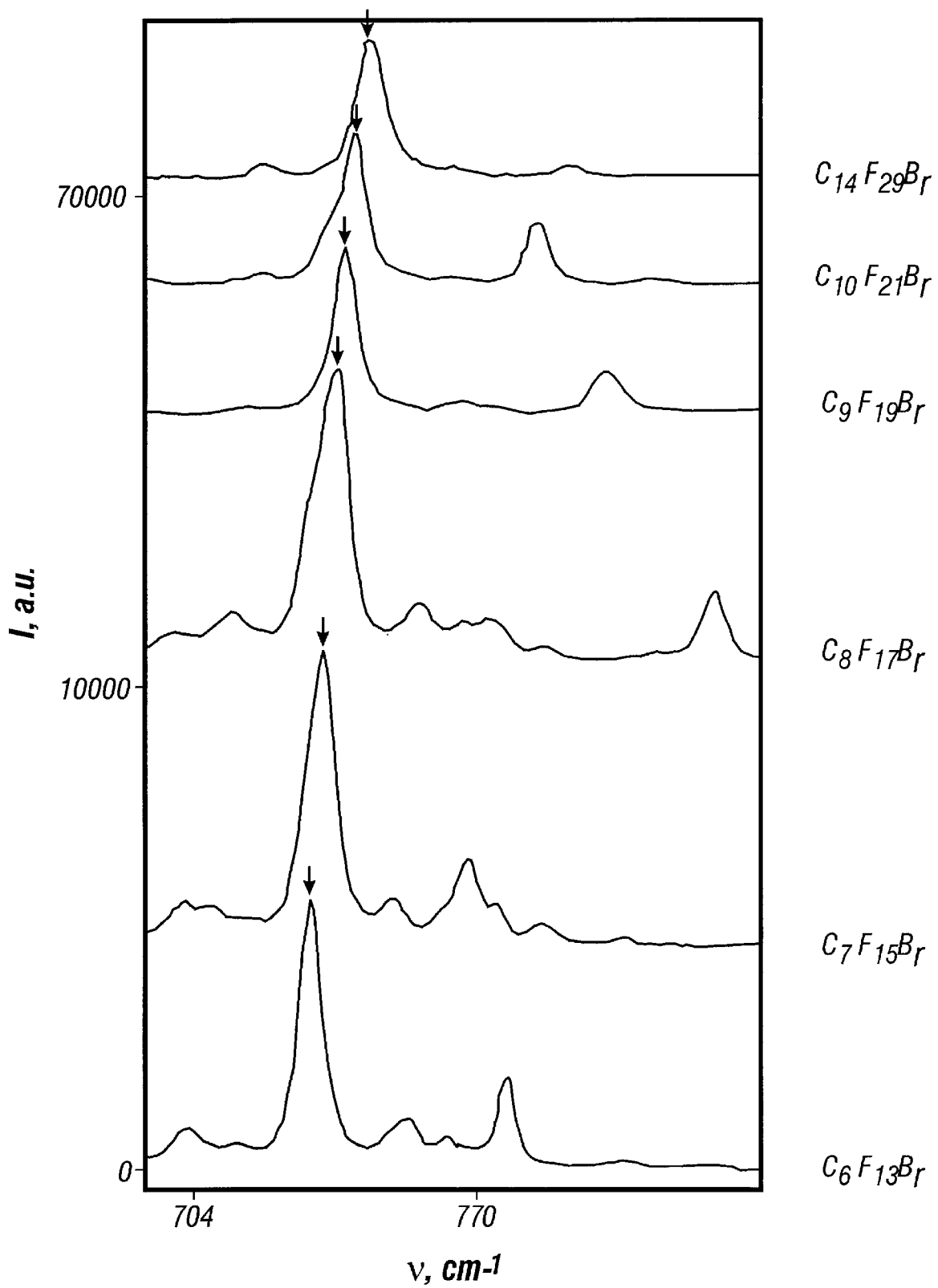
FIG. 13 illustrates the dependency of Raman spectra on the unit length of a molecule in the higher frequency region LOM.

FIGS. 12 and 13 show that lower frequency LAM 80–150 cm$^{-1}$ and higher frequency regions LOM 700–750 cm$^{-1}$ of Raman spectra of $C_nF_{2n+1}Br$ compounds depend on the number of carbons in the molecule chain. The frequency of the LAM decreases as n increases (FIG. 12). However, the frequency of LOM increases when n increases (FIG. 3).

Figure 15:
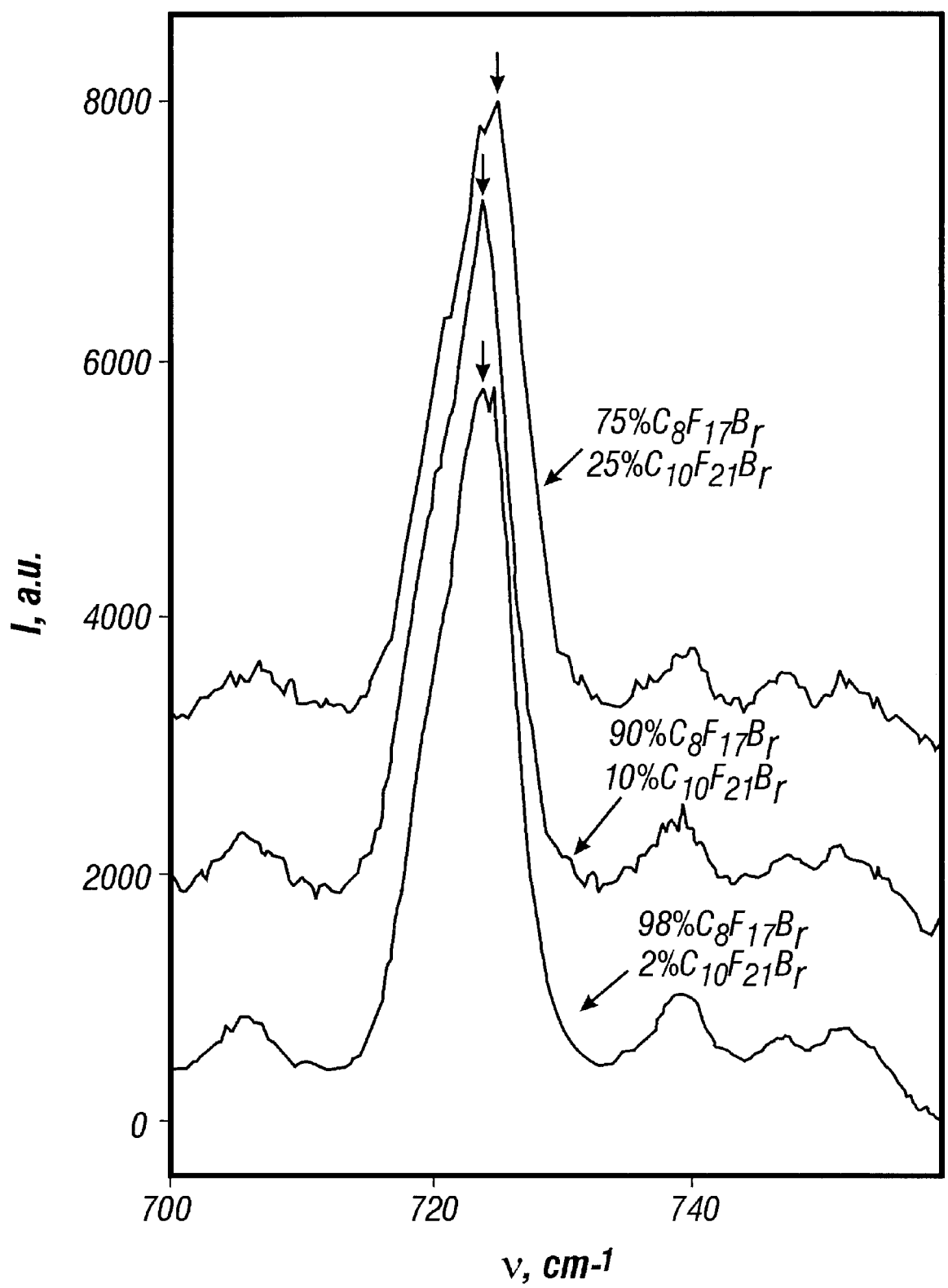
FIG. 15 illustrates the Raman spectra of a two-component mixture of $C_nF_{2n+1}Br$ obtained at three concentrations of components at a Raman signal for a $CF_2$ bond.
Figure 16:
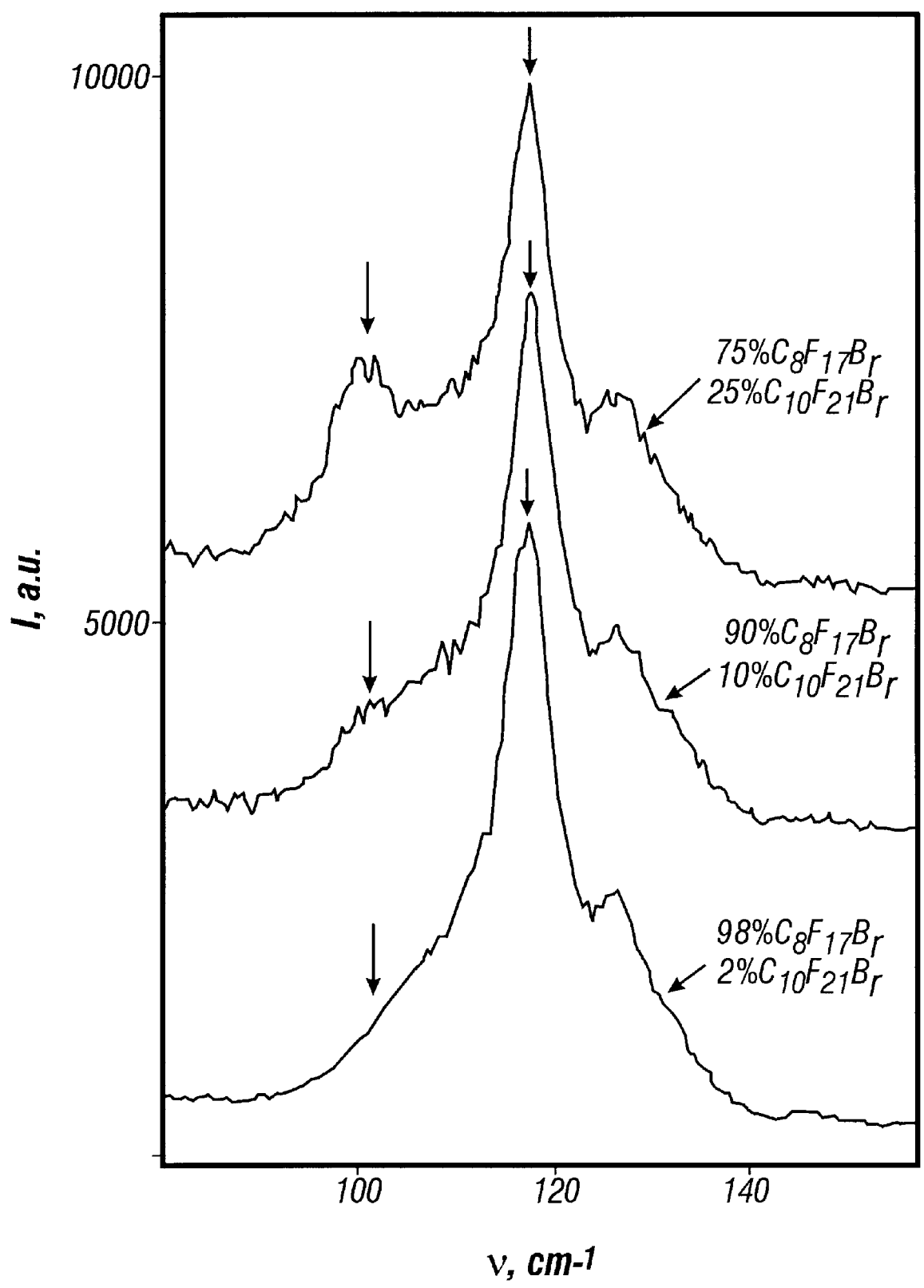
FIG. 16 illustrates the Raman spectra of a two-component mixture of $C_nF_{2n+1}Br$ obtained at three different concentrations of the components at a characteristic Raman signal in the lower frequency region LAM band.

FIGS. 15 and 16 show Raman spectra of mixtures of fluoroorganic compounds in the spectral area characteristic for a $CF_2$ bond and the Raman spectra of such mixtures in the lower frequency region LAM. At a concentration higher than about 2%, the Raman peaks were identified for the certain type of the fluoroorganic compound.

Table 2 below lists Raman spectral data for $C_{12}F_{2n+1}Br$ in the LAM and LOM frequency ranges.

TABLE 2

| Wave number, cm$^{-1}$ | Relative Intensity | Bandwidth, cm$^{-1}$ | Compound |
| --- | --- | --- | --- |
| 77.7 | 3634 | 7.4 | $C_{14}F_{29}Br$ |
| 100.9 | 1236 | 5.4 | $C_{10}F_{21}Br$ |
| 111.4 | 1533 | 7.0 | $C_9F_{19}Br$ |
| 117.5 | 1409 | 6.0 | $C_8F_{17}Br$ |
| 134.6 | 4694 | 7.1 | $C_7F_{15}Br$ |
| 142.1 | 4804 | 6.3 | $C_6F_{13}Br$ |

TABLE 2-continued

| Wave number, cm$^{-1}$ | Relative Intensity | Bandwidth, cm$^{-1}$ | Compound |
| --- | --- | --- | --- |
| 730.3 | 2962 | 5.5 | $C_{14}F_{29}Br$ |
| 727.3 | 2964 | 4.4 | $C_{10}F_{21}Br$ |
| 725.4 | 3398 | 4.7 | $C_9F_{19}Br$ |
| 723.9 | 5310 | 4.7 | $C_8F_{17}Br$ |
| 721.1 | 5048 | 4.1 | $C_7F_{15}Br$ |
| 719.8 | 5567 | 4.2 | $C_6F_{13}Br$ |

Comparison of the different Raman spectra of mixtures of fluororganic compounds indicates that the observed shifts depends on the length of the molecules. The acoustic and optical modes of vibration can be described using the dispersion law as follows:

$$\omega_{acoustic} = 2(S/a) \times \sin^2(ka/2), \quad (1)$$

$$\omega_{optical} = \omega_0^2 - 4(S^2/a^2) \times \sin^2(ka/2), \quad (2)$$

where $\omega_{acoustic}$ is the frequency of the acoustic mode;

$\omega_{optical}$ is the frequency of the optical mode;

k is a vector which has a value of $2\pi/\lambda$, where $\lambda$ is the wavelength;

a is the distance between atoms of a molecule chain;

S is the acoustical propagation speed.

The vector k and the frequencies $\omega_{acoustic}$ and $\omega_{optical}$ can have various discrete values if the length of the molecule chain is finite and has determined limits. Using the shift of the acoustical and optical frequencies and plotting CF molecular length of CF versus the frequency shift, the molecular length ("L") of quasi-linear molecules in mixtures of fluorocarbon molecules can be estimated. Accordingly, the minimum value for the frequencies can be calculated as follows:

For $f = \omega_{acoustic}/2\pi$ at the acoustic mode LAM:

$$f_{acoustic} = 2(S/2\pi a) \times \sin(ka/2) \approx (S/\pi a) \times (a/2L) = (S/2L), \quad (3)$$

where L>>a and $k_{min} = \pi/L$.

For $f = \omega_{optical}/2\pi$ at the optical mode LOM:

$$f_{optical}^2 = f_0^2 - 4(S^2/4\pi^2 a^2) \times \sin^2(\pi a/2L) = f_0^2 - S^2/4L^2, \quad (4)$$

where L is the length of the molecule.

Assuming that $v_0 = \omega_0/2\pi c$, $v = \omega/2\pi c$, and $k_{min} = \pi/L$, where $v$ and $v_0$ are wave numbers, and c is the speed of light, the wavenumber dependencies the length (L) of the molecule for the acoustical ($v_{acoustic}$) and optical ($v_{optical}$) branches can be calculated as:

$$v_{acoustic} = (S/\pi ac) \times \sin(\pi a/2L). \quad (5)$$

$$v_{optical}^2 = v_0^2 - (S^2/\pi^2 a^2 c^2) \times \sin^2(\pi a/2L). \quad (6)$$

Figure 14:
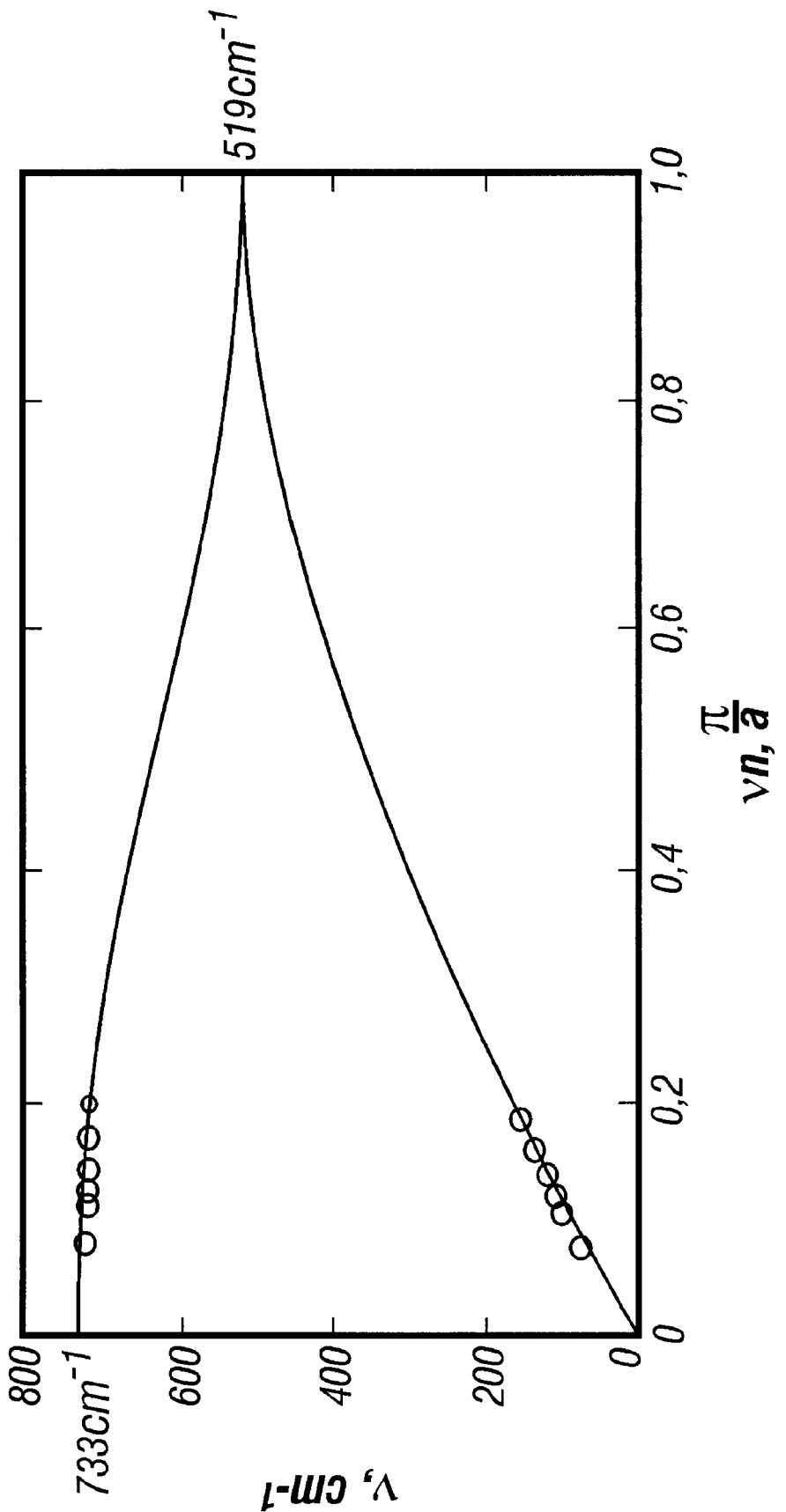
FIG. 14 illustrates experimental Raman frequencies.

FIG. 14 illustrates experimental Raman frequencies indicated by circles for $C_nF_{2n+1}Br$ at n=6, 7, 8, 9, 10, and 14. The experimental frequencies represent the values of the spectra indicated in FIGS. 11–13. FIG. 14 also illustrates calculated frequencies, as indicated by solid lines, that match the above spectra values. These calculations assume that L=na/2, where n is the number of carbons, e.g., 6, 7, 8, 9, 10, and 14. Comparison of the experimental and calculated frequencies indicates that actual Raman frequencies for varying values of n can be accurately calculated using the preferred method.

The dependency of the length of the molecule on the Raman signal has been established in "quasi-onedimensional" molecules of fluororganic compounds. With an increase in the molecular length, the high frequency (optical) mode LOM of $CF_2$ linearly increases, and the lower frequency (acoustical) mode LOM decreased. Accordingly, the length of the molecular species in a mixture using the changing optical and acoustical frequency modes can be approximated.

Sample

The method of the invention can be used to analyze a variety of samples. The method can identify fluoroorganic compounds in liquid, gaseous, crystalline or amorphous solid states or in solutions or suspensions of the fluorooorganic compounds in gases, liquids, solids or multiphase media. The method is more sensitive than other methods for detecting the carbon-fluorine bond of fluoroorganic compounds, permitting detection of fluoroorganic compounds at $10^{-3}$–$10^{-6}$ g/L concentrations level. The background of observation is naturally blank, which permits lower detection limits. The sample can be aqueous solutions of water soluble fluoroorganic compounds including those organic fluorine compounds having low solubility in water or contain traces of water. The method can be used on small solid samples or in solution including aqueous solution. Mixtures can be used when one of the compounds is a fluoroorganic compound, because the unique carbon-fluorine Raman emission, centered around 730 $cm^{-1}$, is characteristic for fluoroorganic compounds.

Thus, the invention permits the analysis of fluoroorganic compounds where the compound is a drug, herbicide on vegetation, or pesticide on vegetation or animals. The method can be used to follow fluorooorganic compounds used as drugs in animals to determine their presence and the presence of metabolites before excretion. Applications include pharmaceutical research and development, drug clinical trials, drug manufacturing, medical and biomedical applications. Also, organic fluorine compounds or derivatives which contaminate the environment can be detected at the nanogram level. Applications include environmental analysis of water, soil and air contaminated with fluorooorganic compounds, continuous monitoring of manufacturing fluorocarbon products and intermediates, and other similar applications. The method is thus useful in quality control for industrial firms working with fluoroorganic compounds. Dielectrics containing carbon-fluorine bonds are a further area of interest. The ultimate environmental fate of many fluorocarbon refrigerants is trifluoroacetic acid, which has been found in wetlands in environmental studies. The method is a superior analytical technique to permit analyzing large numbers of soil samples for trifluoroacetic acid or for agriculture fluorinated pesticides. Moreover, the method can greatly reduce the research cost for developing new fluoroorganic pharmaceutical preparations, herbicides, and pesticides.

Quantitation of fluoroorganic compounds in a sample can be achieved by the method of the invention. When an analyst knows the organic fluorine compound present and measures the number of carbon-fluorine bonds, the molar amount of the fluoroorganic compound can be determined.

The invention has applications with respect to detecting other carbon-halogen bonds, including carbon-chlorine, carbon-bromine, carbon-iodine, and carbon-astatine.

A number of embodiments of the present invention have been described. Nevertheless, it will be understood that various modifications may be made without departing from the spirit and scope of the invention. The copper-vapor laser-based Raman spectrograph described above may find broader applications. Accordingly, other embodiments are within the scope of the following claims.

What is claimed is:

1. A method, comprising:
   providing a sample having a compound including at least one carbon-halogen bond; and
   applying a non-continuous light source to detect the at least one carbon halogen bond.

2. The method of claim 1, wherein the applying the non-continuous light source further comprises exposing the sample to a pulsed metal-vapor laser.

3. The method of claim 1, wherein the at least one carbon-halogen bond comprises at least one carbon-fluorine bond.

4. The method of claim 1, wherein the compound comprises one of Prozac, Prozac substitutes, and Prozac metabolites.

5. The method of claim 1, wherein the compound comprises one of 5-Fluorouracil, 5-Fluorouracil drug substitutes, and 5-Fluorouracil metabolites.

6. The method of claim 1, wherein the compound comprises one of perfluorocarbons and substituted perfluorocarbons.

7. The method of claim 1, wherein the compound comprises fluoropolymer bonds.

8. The method of claim 3, wherein applying a non-continuous light source further comprises applying a metal vapor laser to detect the at least one carbon-fluoride bond.

9. The method of claim 1, wherein the applying the non-continuous light source comprises detecting characteristic Raman scattered light that is indicative of the at least one carbon-halogen bond.

10. The method of claim 1, wherein the non-continuous light source is one of a gold-vapor laser, copper-vapor laser, solid-state laser, and a light bulb.

11. The method of claim 9, wherein the Raman scattered light comprises at least one wave number between approximately 500 $cm^{-1}$ to approximately 800 $cm^{-1}$.

12. The method of claim 9, wherein the applying the non-continuous light source comprises detecting Raman scattered light using a pulse recording system.

13. The method of claim 1, wherein the providing the sample further comprises providing the sample having the compound at approximately $10^3$ to approximately $10^6$ grams/Liter.

14. The method of claim 1, wherein the at least one carbon-halogen bond comprises at least one carbon-fluorine bond and the applying the non-continuous light source comprises detecting a fully symmetric vibrational normal mode of the at least one carbon-fluorine bond.

15. The method of claim 1, wherein the at least one carbon-halogen bond comprises at least one carbon-fluorine bond and the at least one carbon-fluorine bond comprises one of at least one trifluoromethyl group, at least one monofluoromethyl group, at least one difluromethylene group, and at least one fluorinated amino acid.

16. The method of claim 1, wherein applying the non-continuous light source further comprises a wavelength that induces Raman scattered light emissions from the at least one carbon-halogen bond.

17. The method of claim 16, wherein the wavelength is one of approximately 510.6 nm, approximately 578.2 nm, and approximately 627.8 nm.

18. The method of claim 1, wherein the applying the non-continuous light source further comprises time-gating the non-continuous light source.

19. A method, comprising:
   providing at least one fluororganic compound;
   applying a light source to the at least one fluororganic compound determining at least one Raman frequency of an acoustic mode of the at least one fluororganic compound;

determining at least one Raman frequency of an optical mode of the at least one fluororganic compound; and determining a presence of the at least one fluororganic compound as a function of one of the at least one Raman frequency of the acoustic mode and the at least one Raman frequency of the optical mode.

20. The method of claim 19, wherein the determining the presence further comprises determining one of a concentration and a molecular length of the at least one fluororganic compound.

21. The method of claim 19, wherein the light source is a metal-vapor laser.

22. The method of claim 19, wherein the at least one fluoroorganic compound is one of quasi-linear and quasi-one-dimensional.

23. The method of claim 19, wherein the at least one fluoroorganic compound comprises a substitution group.

24. The method of claim 19, wherein the frequency of the acoustic mode decreases with an increase of carbons in the at least one fluoroorganic compound.

25. The method of claim 19, wherein the frequency of the optical mode increases with a decrease of carbons in the at least one fluoroorganic compound.

26. The method of claim 19, wherein the light source comprises a non-continuous light source.

27. The method of claim 19, wherein the light source comprises one of a gold-vapor laser, copper-vapor laser, solid-state laser, and a light bulb.

28. A method, comprising:

causing a sample to emit Raman scattered light;

detecting Raman scattered light indicative of a compound having at least one carbon-halogen bond; and identifying the compound in the sample.

29. The method of claim 28, wherein the at least one carbon-halogen bond comprises at least one carbon-fluorine bond.

30. The method of claim 28, wherein the causing the sample further comprises exposing the sample to a non-continuous light source.

31. The method of claim 30, wherein the light source comprises one of a metal-vapor laser, gold-vapor laser, copper-vapor laser, solid-state laser, and a light bulb.

32. The method of claim 30, wherein the causing the sample further comprises time-gating the non-continuous light source.

33. A method, comprising:

detecting at least one carbon-fluorine bond in one of a drug, a biologically active compound, and a biologically active substance;

introducing the one of the drug, the biologically active compound, and the biologically active substance to a biological media; and determining at least one Raman frequency emitted from one of the drug, the biologically active compound, and the biologically active substance through the biological media.

34. The method of claim 33, wherein the determining the at least one Raman frequency further comprises exposing a sample of the biological media to an excitation light source to determine the at least one Raman frequency.

35. The method of claim 34, wherein the determining the at least one Raman frequency further comprises irradiating the sample with a non-continuous light source.

36. The method of claim 34, wherein the light source is one of a metal-vapor laser, gold-vapor laser, copper-vapor laser, solid-state laser, and a light bulb.

37. The method of claim 33, wherein the drug comprises one of Prozac, Prozac drug substitutes, and Prozac metabolites.

38. The method of claim 33, wherein the drug comprises one of 5-Fluorouracil, Fluorouracil drug substitutes, and Fluorouracil metabolites.

39. The method of claim 33, wherein the drug comprises one of perfluorocarbons and substituted perfluorocarbons.

40. A method, comprising:

detecting at least one carbon-fluorine bond in a blood substitute;

introducing the blood substitute to a biological media; and determining at least one Raman frequency emitted from the blood substitute through the biological media.

41. The method of claim 40, wherein the determining the at least one Raman frequency further comprises exposing a sample of the biological media to an excitation light source to determine the at least one Raman frequency.

42. The method of claim 41, wherein the exposing the sample further comprises irradiating the sample with a non-continuous light source.

43. The method of claim 41, wherein the light source is one of a metal-vapor laser, gold-vapor laser, copper-vapor laser, solid-state laser, and a light bulb.

44. A method, comprising:

introducing at least one carbon-fluorine bond to one of a compound and a substance;

detecting the least one carbon-fluorine bond; and using the at least one carbon-fluorine bond as a tracer.

45. The method of claim 44, wherein the detecting of the at least one carbon-fluorine bond comprises:

exposing one of the substance and the compound to an excitation light source having a wavelength that induces Raman scattered light emission from the at least one carbon-fluorine bond; and detecting Raman scattered light emitted from one of the substance and the compound.

46. The method of claim 44, wherein the exposing one of the substance and the compound further comprises irradiating one of the substance and the compound with a non-continuous light source.

47. The method of claim 45, wherein the light source is one of a metal-vapor laser, gold-vapor laser, copper-vapor laser, solid-state laser, and a light bulb.

48. A method, comprising:

detecting at least one carbon-fluorine bond in a sample;

using the at least one carbon-fluorine bond in the sample as a label;

determining at least one concentration level for one of water, soil, and air samples using the label.

49. The method of claim 48, wherein the detecting the at least one carbon-fluorine bond comprises:

exposing the sample to an excitation light source having a wavelength that induces Raman scatter light emission from the at least one carbon-fluorine bond; and detecting Raman scattered light emitted from the sample, wherein detection of characteristic Raman scattered light is indicative of the at least one carbon-fluorine bond in the sample.

50. The method of claim 49, wherein the exposing the sample further comprises irradiating the sample with a non-continuous light source.

51. The method of claim 49, wherein the light source is one of a metal-vapor laser, gold-vapor laser, copper-vapor laser, solid-state laser, and a light bulb.

52. A method, comprising:

introducing at least one carbon-fluorine bond to a drug;

detecting the at least one carbon-fluorine bond in the drug; and using the at least one carbon-fluorine bond as a label.

53. The method of claim 52, wherein the detecting the at least one carbon fluorine bond further comprises exposing the drug to an excitation light source to determine at least one Raman frequency.

54. The method of claim 53, wherein exposing the sample further comprises irradiating the sample with a non-continuous light source.

55. The method of claim 53, wherein the light source is one of a metal-vapor laser, gold-vapor laser, copper-vapor laser, solid-state laser, and a light bulb.

56. A method, comprising:

exposing a sample to a pulsed metal-vapor laser having a wavelength that induces Raman scattered light emission from at least one carbon-fluorine bond;

time-gating the pulsed metal-vapor laser; and detecting Raman scattered light emitted from a compound in the sample, wherein detection of characteristic Raman scattered light is indicative of at least one carbon-fluorine bond of the compound.

57. The method of claim 56, wherein the metal-vapor laser is one of a copper-vapor laser and a gold-vapor laser.

58. The method of claim 56, wherein the detecting of Raman scattered light comprises detecting the Raman scattered light using a photomultiplier.

* * * * *